(12) United States Patent
Wang et al.

(10) Patent No.: US 7,943,731 B1
(45) Date of Patent: May 17, 2011

(54) DIMERIZING PEPTIDES

(75) Inventors: Bryan S. Wang, Belmont, MA (US); Carl O. Pabo, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1870 days.

(21) Appl. No.: 09/636,243

(22) Filed: Aug. 10, 2000

Related U.S. Application Data

(60) Provisional application No. 60/148,422, filed on Aug. 11, 1999.

(51) Int. Cl.
*C07K 14/00* (2006.01)
*C07H 21/04* (2006.01)

(52) U.S. Cl. ....... 530/350; 530/300; 536/23.1; 536/23.4

(58) Field of Classification Search ............... 435/69.7, 435/69.1, 66; 536/23.4, 23.1; 530/350, 300
See application file for complete search history.

(56) References Cited

U.S. PATENT DOCUMENTS

| | | | | |
|---|---|---|---|---|
| 6,242,568 B1 * | 6/2001 | Barbas et al. | ............... | 530/350 |
| 6,453,242 B1 * | 9/2002 | Eisenberg et al. | ............... | 435/6 |
| 6,479,626 B1 * | 11/2002 | Kim et al. | ............... | 530/300 |
| 6,534,261 B1 * | 3/2003 | Cox et al. | ............... | 435/6 |

FOREIGN PATENT DOCUMENTS

| | | |
|---|---|---|
| WO | WO 98/53058 | 11/1998 |
| WO | WO 98/53059 | 11/1998 |
| WO | WO 98/53060 | 11/1998 |
| WO | WO 00/41566 | 7/2000 |
| WO | WO 00/42219 | 7/2000 |

OTHER PUBLICATIONS

Zaid, Glossary of biotechnology and genetic engineering, FAO Research & Technology Paper, 158 (1999).*
Krylov, The EMBO Journal, 13(12):2849-61 (1994).*
Marmostein et al., Nature, 1992, 356, 408-413.*
Choo et al., "In Vivo Repression by a Site-Specific DNA-Binding Protein Designed Against an Oncogenic Sequence," *Nature* 372:642-645 (1994).
Choo et al., "Toward a Code for the Interactions of Zinc Fingers with DNA: Selection of Randomized Fingers Displayed on Phage," *PNAS* 91:11163-11167 (1994).
Greisman & Pabo, "A General Strategy for Selecting High-Affinity Zinc Finger Proteins for Diverse DNA Target Sites," *Science* 275:657-661 (1997).
Isalan et al., Synergy Between Adjacent Zinc Fingers in Sequence-Specific DNA Recognition, *PNAS* 94:5617-5621 (1997).
Jamieson et al., "In Vitro Selection of Zinc Fingers with Altered DNA-Binding Specificity," *Biochemistry* 33:5689-5695 (1994).
Kim and Pabo, "Getting a Handhold on DNA: Design of Poly-Zinc Finger Proteins with Femtomolar Dissociation Constants," *Proc. Natl. Acad. Sci. U.S.A.* 95:2812-2817 (1998).
Kim and Pabo, "Transcriptional Repression by Zinc Finger Peptides," *The Journal of Biological Chemistry* 272(47):29795-29800 (1997).
Liu et al., "Design of Polydactyl Zinc-Finger Proteins for unique Addressing Within Complex Genomes," *PNAS* 94:5525-5530 (1997).
Pomerantz et al., "Structure-Based Design of Transcription Factors," *Science* 267:93-96 (1995).
Pomerantz et al., "Structure-Based Design of Dimeric Zinc Finger Protein," *Biochemistry* 37(4):965-970 (1998).
Rebar et al., "Phage Display Methods for Selecting Zinc Finger Proteins with Novel DNA-Binding Specificities," *Methods in Enzymology* 267:129-149 (1996).
Rebar et al., "Zinc Finger Phage: Affinity Selection of Fingers with New DNA-Binding Specificities," *Science* 263:671-673 (1994).
Wolfe et al. "Analysis of Zinc Fingers Optimized via Phage Display: Evaluating the Utility of a Recognition Code," *Journal of Mol. Biol.* 285:1917-1934 (1999).

* cited by examiner

*Primary Examiner* — T. D. Weswendorf
(74) *Attorney, Agent, or Firm* — Dahna S. Pasternak; Robins & Pasternak LLP

(57) ABSTRACT

The invention provides nonnaturally occurring dimerizing peptides, and methods for their production. Such peptides are useful to mediate association of linked functional proteins domains. In particular, such peptides are useful for mediating association of complexes of multiple zinc finger proteins thereby affording greater specificity and/or affinity in binding of the zinc finger proteins to proximately spaced target segments.

4 Claims, 9 Drawing Sheets

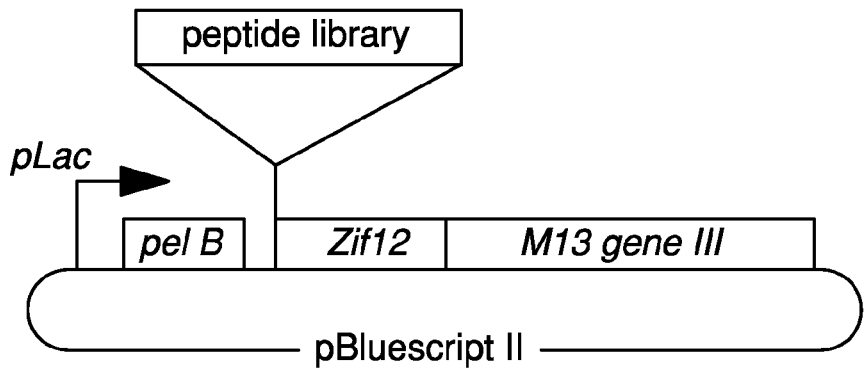
FIG. 3A
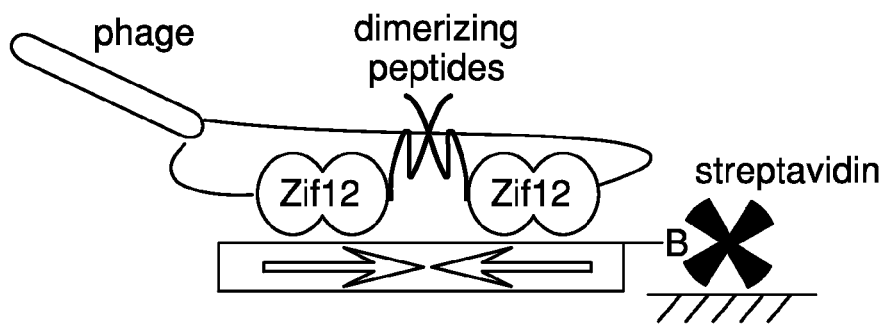
FIG. 3B
```
5'-GCAG TGGGCGCGCCCA CAGTACTTGAACGTAACG— Bio
3'-CGTC ACCCGCGCGGGT GTCATGAACTTGCATTGC
```
FIG. 3C

FIG. 4A  peptide 1: GGGQWLGTWEWYGPK (10)
2: YEKISVEGIKDVRVR (9)
3: NVSIEGVLKYYRGLR (6)
4: RSCGLDYEGYWLKLK (13)
5: SRWLEEEVSRLLLLR (6)
6: GEALDRFEREMKLMR (1)

*peptide 1*  GGGQW LGTWE WYGPK – Zif12

Step 1
(Cycle 6)
GGGQW LGTWE HPKMK
GGGQW LGTWE PAKIR
GGGQW LGTWE VPKSR
GGGQW LGTWE VPRLK
GGGQW LGTWE APKLR
GGGQW LGTWE HAKIR
GGGQW LGTWE VVKMR
GGGQW LGTWE PVKMR

E21D
GGGQW LGTWE VPKQR

Step 1
(Cycle 9)
GGGQW LLNYK VPKQR
GGGQW LLNYV VPKQR
GGGQW LIDYI VPKQR
GGGQW LLNYI VPKQR
GGGQW LLQYV VPKQR
GGGQW LLNYV VPKQR
GGGQW LLEYK VPKQR
GGGQW LLDYV VPKQR Step 2
(Cycle 9)
GGGQW LLNYV VPKMR
GGGQW LLNYV VPKMR
GGGQW LLNYV VPKQR
GGGQW LLNYV VPKMR
GGGQW LLNYV VPKLR
GGGQW LLNYV VPKLR
GGGQW LLNYV VPKLR
GGGQW LLNYV VPKLR Step 3
(Cycle 6)
HPMNN LLNYV VPKMR
HPMNN LLNYV VPKMR
PPSTE LLNYV VPKLR
QKYGD LLNYV VPKLR
ENYEK LLNYV VPKLR
ENYEK LLNYV VPKLR
LLNYV VPKLR
LLNYV VPKLR

*peptide 1\**  HPMNN LLNYV VPKMR – Zif12

*peptide 1\**  ENYEK LLNYV VRKLR – Zif12
*(variant)*

---

*peptide 5*  SRWLE EEVSR LLLLR – Zif12

Step 1
(Cycle 9)
FRWLE EEVSR MRLWR
FRWLE EEVSR MRGWK
FRWLE EEVSR MRGWK
SRWLE EEVSR MRKWR
SRWLE EEVSR MRKWR
SRWLE EEVSR MRKWR
SRWLE EEVSR MRKWK
SRWLE EEVSR MGVMR

E21D
SRWLE EYLES MRKWR

Step 2
(Cycle 6)
SRWLE EYLES MRKWR
SRWLE DYVTQ MRKWR
SRWLE DYLAD MRKWR
SRWLE EYLTF MRKWR
SRWLE QYLED MRKWR
SRWLE DYVSQ MRKWR
SRWLE SYLDK MRKWR
SRWLE EYMSD MRKWR Step 3
(Cycle 6)
QPWLT EYLES MRKWR
PPWLT EYLES MRKWR
PPWLK EYLES MRKWR
PAWLT EYLES MRKWR
PAWLA EYLES MRKWR
WAWLD EYLES MRKWR
PPWLK EYLES MRKWR
PTWLK EYLES MRKWR

*peptide 5\**  PAWLT EYLES MRKWR – Zif12

FIG. 6

```
ZIF1: P Y A C P V K S C D R R F S R S D E L T R K T R I R T
GLI1: E T D C F W D G C S Q E F D S Q E Q L V K H I N SEH I
GLI2: K K V C F W G G C SKELRFF K A Q Y M L V V M M K R H T
SWI1: T K E C L F K C C T K T F K K K Y N L R C M I Q T H L
```

DIMERIZING PEPTIDES

CROSS-REFERENCES TO RELATED APPLICATIONS

The present application derives priority from U.S. Ser. No. 60/148,422 filed Aug. 11, 1999, which is incorporated by reference in its entirety for all purposes.

TECHNICAL FIELD

The invention resides in the technical field of protein engineering.

BACKGROUND OF THE INVENTION

Zinc finger proteins (ZFPs) are proteins that can bind to DNA in a sequence-specific manner. Zinc fingers were first identified in the transcription factor TFIIIA from the oocytes of the African clawed toad, Xenopus laevis. An exemplary motif characterizing one class of these protein ($C_2H_2$ class) is -Cys-(X)$_{2-4}$-Cys-(X)$_{12}$-His-(X)$_{3-5}$-His (where X is any amino acid) (SEQ ID NO:1). A single finger domain is about 30 amino acids in length, and several structural studies have demonstrated that it contains an alpha helix containing two invariant histidine residues and two invariant cysteine residues in a beta turn co-ordinated through zinc. To date, over 10,000 zinc finger sequences have been identified in several thousand known or putative transcription factors. Zinc finger domains are involved not only in DNA-recognition, but also in RNA binding and in protein-protein binding. Current estimates are that this class of molecules will constitute about 2% of all human genes.

The x-ray crystal structure of Zif268, a three-finger domain from a murine transcription factor, has been solved in complex with a cognate DNA-sequence and shows that each finger can be superimposed on the next by a periodic rotation. The structure suggests that each finger interacts independently with DNA over 3 base-pair intervals, with side-chains at positions −1, 2, 3 and 6 on each recognition helix making contacts with their respective DNA triplet subsites. The amino terminus of Zif268 is situated at the 3' end of the DNA strand with which it makes most contacts. Recent results have indicated that some zinc fingers can bind to a fourth base in a target segment (Isalan et al., PNAS 94, 5617-5621 (1997)). If the strand with which a zinc finger protein makes most contacts is designated the target strand, some zinc finger proteins bind to a three base triplet in the target strand and a fourth base on the nontarget strand. The fourth base is complementary to the base immediately 3' of the three base subsite.

The structure of the Zif268-DNA complex also suggested that the DNA sequence specificity of a zinc finger protein might be altered by making amino acid substitutions at the four helix positions (−1, 2, 3 and 6) on each of the zinc finger recognition helices. Phage display experiments using zinc finger combinatorial libraries to test this observation were published in a series of papers in 1994 (Rebar et al., Science 263, 671-673 (1994); Jamieson et al., Biochemistry 33, 5689-5695 (1994); Choo et al, PNAS 91, 11163-11167 (1994)). Combinatorial libraries were constructed with randomized side-chains in either the first or middle finger of Zif268 and then used to select for an altered Zif268 binding site in which the appropriate DNA sub-site was replaced by an altered DNA triplet. Further, correlation between the nature of introduced mutations and the resulting alteration in binding specificity gave rise to a partial set of substitution rules for design of ZFPs with altered binding specificity.

Greisman & Pabo, Science 275, 657-661 (1997) discuss an elaboration of the phage display method in which each finger of a Zif268 was successively randomized and selected for binding to a new triplet sequence. This paper reported selection of ZFPs for a nuclear hormone response element, a p53 target site and a TATA box sequence.

A number of papers have reported attempts to produce ZFPs to modulate particular target sites. For example, Choo et al., Nature 372, 645 (1994), report an attempt to design a ZFP that would repress expression of a brc-abl oncogene. The target segment to which the ZFPs would bind was a nine base sequence 5' GCA GAA GCC3' chosen to overlap the junction created by a specific oncogenic translocation fusing the genes encoding brc and abl. The intention was that a ZFP specific to this target site would bind to the oncogene without binding to abl or brc component genes. The authors used phage display to screen a mini-library of variant ZFPs for binding to this target segment. A variant ZFP thus isolated was then reported to repress expression of a stably transfected brc-able construct in a cell line.

Pomerantz et al., Science 267, 93-96 (1995) reported an attempt to design a novel DNA binding protein by fusing two fingers from Zif268 with a homeodomain from Oct-1. The hybrid protein was then fused with a transcriptional activator for expression as a chimeric protein. The chimeric protein was reported to bind a target site representing a hybrid of the subsites of its two components. The authors then constructed a reporter vector containing a luciferase gene operably linked to a promoter and a hybrid site for the chimeric DNA binding protein in proximity to the promoter. The authors reported that their chimeric DNA binding protein could activate expression of the luciferase gene.

Liu et al., PNAS 94, 5525-5530 (1997) report forming a composite zinc finger protein by using a peptide spacer to link two component zinc finger proteins each having three fingers. The composite protein was then further linked to transcriptional activation domain. It was reported that the resulting chimeric protein bound to a target site formed from the target segments bound by the two component zinc finger proteins. It was further reported that the chimeric zinc finger protein could activate transcription of a reporter gene when its target site was inserted into a reporter plasmid in proximity to a promoter operably linked to the reporter.

Choo et al., WO 98/53058, WO98/53059, and WO 98/53060 (1998) discuss selection of zinc finger proteins to bind to a target site within the HIV Tat gene. Choo et al. also discuss selection of a zinc finger protein to bind to a target site encompassing a site of a common mutation in the oncogene ras. The target site within ras was thus constrained by the position of the mutation.

The present application is related to copending application Ser. No. 09/229,007 filed Jan. 12, 1999 (WO 00/42219), now U.S. Pat. No. 6,453,242 and 09/229,037 filed Jan. 12, 1999 (WO 00/41566), and both incorporated by reference in their entirety for all purposes.

SUMMARY OF THE CLAIMED INVENTION

The invention provides nonnaturally occurring dimerizing peptides. Some such peptides are homo-dimerizing peptides. Such peptides typically lack significant sequence identity with a naturally occurring peptide. Some peptides have a length of 30 amino acids or shorter.

The invention also provides zinc finger complexes. Such a complex comprises a first fusion protein comprising a first zinc finger protein and a first peptide linker and a second fusion protein comprising a second zinc finger protein and a second peptide linker. The first and second fusion proteins are complexed by specific binding of the first and second peptide linkers, and the first and second peptide linkers are nonnaturally occurring peptides. In some complexes, the first and second peptide linkers are first and second copies of the same linker.

The invention further provides methods of selecting a dimerizing peptide. Such methods entail providing a phage display library in which a member displays a zinc finger protein fused to a peptide from its outersurface, the zinc finger protein being the same in different members, and the peptide varying between different members. The library is then contacted with a nucleic acid substrate comprising first and second binding sites for the zinc finger protein. Phage displaying a zinc finger protein fused to a dimerizing peptide preferentially bind to the substrate relative to phage displaying a zinc fusion protein fused to a nondimerizing peptide. The phage that bind to the substrate are isolated. A segment of the genome of a phage binding to the substrate is sequenced to determine the identity of a dimerizing peptide. In some such methods, the first and second binding sites are in opposing orientations in the substrate. In some methods, the phage displaying a zinc finger protein fused to a dimerizing peptide bind to the substrate via display of two copies of the zinc finger protein and the dimerizing peptide, whereby the two copies of the zinc finger protein respectively bind to the first and second binding sites, and the two copies of the dimerizing peptide bind to each other. In some methods, the peptide is a random peptide. In some methods, the peptide is 30 amino acids or fewer in length.

The invention further provides methods of regulating or detecting a target sequence. Such methods entail contacting the target sequence with a zinc finger complex, comprising a first fusion protein comprising a first zinc finger protein that specifically binds a segment of the target sequence and a first peptide linker and a second fusion protein comprising a second zinc finger protein that specifically binds a second segment of the target sequence and a second peptide linker. The first fusion protein binds to the first segment of the target sequence, and the second fusion protein binds to the second segment of the target sequence, and the first and second fusion proteins bind to each other via the first and second peptides. In some such methods, the target sequence is present in an intact cell. Some such methods further comprise contacting the cell with an expression vector encoding the first fusion protein and/or the second fusion protein, wherein the expression vector enters the cell and is expressed to produce the first and/or second fusion protein. In some methods, the target sequence is present in a patient. In some methods, the target sequences is present in a cell extract.

BRIEF DESCRIPTION OF THE DRAWINGS

FIG. 3(A) Sketch showing key segments of the phagemid. (B) Expected arrangement of fusion proteins at the target DNA. Phage displaying two copies of a dimerizing peptide-Zif12 fusion can form stable complexes with the biotinylated target DNA site, which contains an inverted repeat of the Zif12-binding site. The phage-DNA complexes are captured by streptavidin coupled to a solid support, and phage that bind less tightly are washed away. (C) The DNA site (SEQ ID NO:23) used for affinity selection of phage, with the two juxtaposed Zif12-binding sites in bold.

FIG. 6. Evolution of peptides 1 and 5 by sequential block reoptimization (SEQ ID NOS:30-79). The sequences selected from each reoptimization step are shown in bold, with the number of selection and amplification cycles given in parentheses. Sequences roughly matching the consensus that were used in later steps have been boxed. In some cases, such as in reoptimization step 3 for peptide 1 and reoptimization step 1 for peptide 5, we isolated clones that carried spurious mutations at a nondegenerate position of the peptide extension. In addition, the E21D mutation in the zinc finger region (which also was seen in the original peptide 2 sequence) arose several times; this mutation may stabilize complex formation by improving contacts at the protein-DNA interface. Note: some confusion was caused by this E21D mutation, which occurred in the first reoptimization step for peptide 1, but was discovered only after reoptimization step 2. Thus, the "consensus" sequence from reoptimization step 1 (VPKQR (SEQ ID NO:53)), chosen after selection-amplification cycle 9, had a glutamine that did not occur in sequences isolated after cycle 6. To double-check this position of peptide 1, it was randomized again during reoptimization step 3. The corresponding position was allowed to vary as Q, M, I, or L, along with the complete randomization of the third block. The reselections showed that methionine or leucine is preferred at this position.

DEFINITIONS

Figure 1:
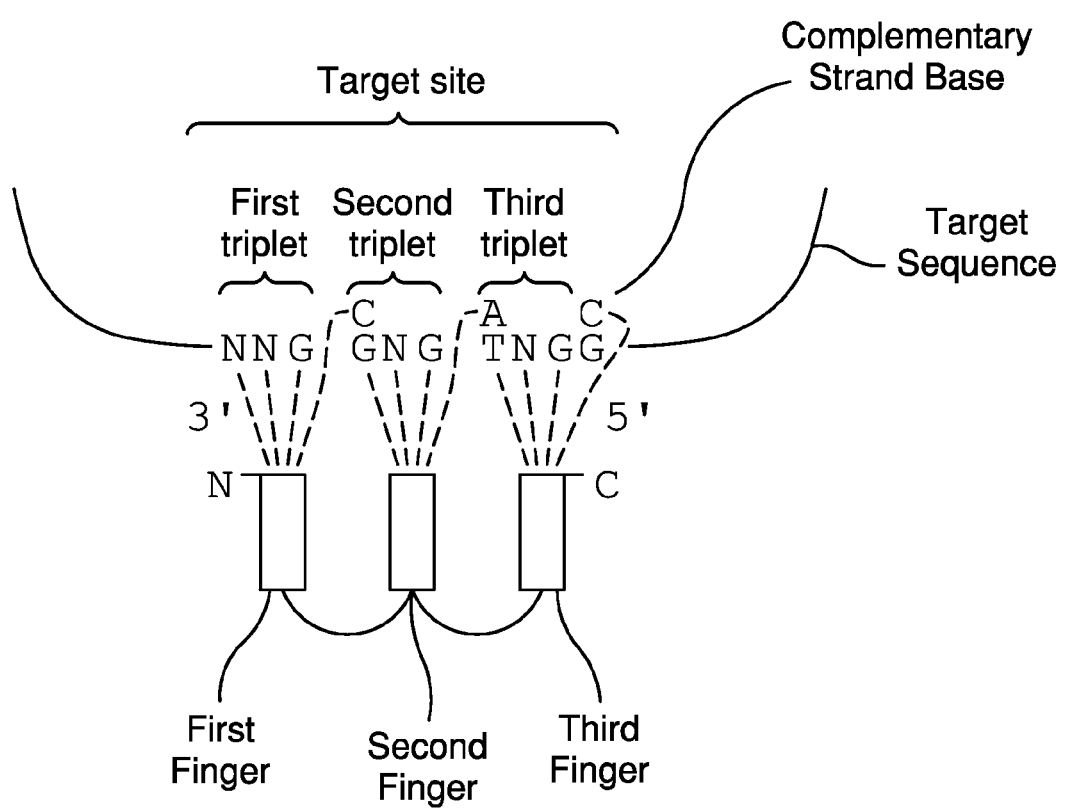
FIG. 1 shows a three finger zinc finger protein bound to a target site containing three D-able subsites.

A zinc finger DNA binding protein is a protein or segment within a larger protein that binds DNA in a sequence-specific manner as a result of stabilization of protein structure through coordination on of zinc ion. The term zinc finger DNA binding protein is often abbreviated as zinc finger protein or ZFP.

A designed zinc finger protein is a protein not occurring in nature whose design/composition results principally from rational criteria. Rational criteria for design include application of substitution rules and computerized algorithms for processing information in a database storing information of existing ZFP designs and binding data.

A selected zinc finger protein is a protein not found in nature whose production results primarily from an empirical process such as phage display.

The term naturally-occurring is used to describe an object that can be found in nature as distinct from being artificially produced by man. For example, a polypeptide or polynucleotide sequence that is present in an organism (including viruses) that can be isolated from a source in nature and which has not been intentionally modified by man in the laboratory is naturally-occurring. Generally, the term naturally-occurring refers to an object as present in a non-pathological (undiseased) individual, such as would be typical for the species.

Conversely, the term nonnaturally-occurring is used to describe objects and sequences not found in nature. Preferred nonnaturally occurring sequences show no significant sequence identity, e.g., less than 50% (amino acid or nucleotide) with natural sequences, in distinction from induced mutations of natural sequences. Typically, nonnaturally occurring sequences do not contain a contiguous segment of at least half their length with a natural protein. Some nonnaturally occurring peptides fold in conformations distinct from natural peptides. Some nonnaturally occurring sequences are selected from random peptide libraries.

Random peptide refers to an oligomer composed of two or more amino acid monomers and constructed by a means with which one does not entirely preselect the complete sequence of a particular oligomer.

A random peptide library refers not only to a set of recombinant DNA vectors (also called recombinants) that encodes a set of random peptides, but also to the set of random peptides encoded by those vectors, as well as the set of fusion proteins containing those random peptides. Random peptide libraries frequently contain as many as $10^6$ to $10^{12}$ different compounds.

A nucleic acid is operably linked when it is placed into a functional relationship with another nucleic acid sequence. For instance, a promoter or enhancer is operably linked to a coding sequence if it increases the transcription of the coding sequence. Operably linked means that the DNA sequences being linked are typically contiguous and, where necessary to join two protein coding regions, contiguous and in reading frame. However, since enhancers generally function when separated from the promoter by up to several kilobases or more and intronic sequences may be of variable lengths, some polynucleotide elements may be operably linked but not contiguous.

A specific binding affinity between, for example, a ZFP and a specific target site means a binding affinity of at least $1 \times 10^6 \, M^{-1}$.

The terms "modulating expression" "inhibiting expression" and "activating expression" of a gene refer to the ability of a zinc finger protein to activate or inhibit transcription of a gene. Activation includes prevention of subsequent transcriptional inhibition (i.e., prevention of repression of gene expression) and inhibition includes prevention of subsequent transcriptional activation (i.e., prevention of gene activation). Modulation can be assayed by determining any parameter that is indirectly or directly affected by the expression of the target gene. Such parameters include, e.g., changes in RNA or protein levels, changes in protein activity, changes in product levels, changes in downstream gene expression, changes in reporter gene transcription (luciferase, CAT, beta-galactosidase, GFP (see, e.g., Mistili & Spector, *Nature Biotechnology* 15:961-964 (1997)); changes in signal transduction, phosphorylation and dephosphorylation, receptor-ligand interactions, second messenger concentrations (e.g., cGMP, cAMP, IP3, and Ca2+), cell growth, neovascularization, in vitro, in vivo, and ex vivo. Such functional effects can be measured by a conventional methods, e.g., measurement of RNA or protein levels, measurement of RNA stability, identification of downstream or reporter gene expression, e.g., via chemiluminescence, fluorescence, colorimetric reactions, antibody binding, inducible markers, ligand binding assays; changes in intracellular second messengers such as cGMP and inositol triphosphate (IP3); changes in intracellular calcium levels; cytokine release, and the like.

A "regulatory domain" refers to a protein or a protein subsequence that has transcriptional modulation activity. Typically, a regulatory domain is covalently or non-covalently linked to a ZFP to modulate transcription. Alternatively, a ZFP can act alone, without a regulatory domain, or with multiple regulatory domains to modulate transcription.

A D-able subsite within a target site has the motif 5'NNGK3' (SEQ ID NO:2). A target site containing one or more such motifs is sometimes described as a D-able target site. A zinc finger appropriately designed to bind to a D-able subsite is sometimes referred to as a D-able finger. Likewise a zinc finger protein containing at least one finger designed or selected to bind to a target site including at least one D-able subsite is sometimes referred to as a D-able zinc finger protein.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul (1993) Proc. Nat'l. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

DETAILED DESCRIPTION

I. General

The application provides methods for selecting dimerization peptides that mediate association of linked functional proteins domains. The peptides can mediate such association by homodimerizing with each other, by heterodimerizing with the linked protein domains, or by binding to an entity, such as a DNA target site, itself bound by the linked protein domains. In particular, such peptides are useful for mediating association of complexes of multiple zinc finger proteins thereby affording greater specificity and/or affinity in binding of the zinc finger proteins to proximately spaced target segments.

Dimerizing peptides can be selected from a phage display library among other methods. A phage or phagemid vector is genetically engineered so that phage particles displaying a zinc finger protein fused to a peptide being screened are displayed from the outersuface of the phage fused to a phage coat protein. Typically, the same zinc finger protein is displayed from each phage. The peptide being screened varies between phage. Typically, the peptides constitute a random peptide library. The peptide size can vary from about 2-500 amino acids, with sizes of 8-25 amino acids being preferred. Typical libraries contain $10^6$-$10^{10}$ members.

Libraries are screened by contacting the library with a nucleic acid target containing two binding segments for the zinc finger protein displayed by the phage. Typically, the two binding segments are in opposing orientations (i.e., the 5'-3-strand of one segment is the 3'5' segment of the other, and vice versa). Although an understanding of mechanism is not required for practice of the invention, it is believed that phage displaying two copies of the zinc finger protein and linked peptide can bind to the target via both specific bonding of each copy of the protein to a respective target segment, and supporting interactions made by the peptides. Such supporting interactions can include contacts between the peptides and/or contacts between a peptide and another region of the protein (e.g., an adjacent zinc finger), and can also be stabilized by peptide-DNA contacts. Contacts between peptides and adjacent zinc fingers are facilitated by a hydrophobic batch on the surface of zinc finger The resulting arrangement in which a phage is effectively chelated to the target segment provides substantially stronger binding than can be mediated by phage lacking a dimerizing peptide. When the peptide-ZFP fusions displayed by such phage are purified, they are able to bind more tightly to the target sequence than the zinc finger portions alone. Accordingly, conditions of appropriate stringency can be devised such that phage displaying a zinc finger protein and dimerizing peptide can be selectively enriched and separated from other phage lacking such a peptide.

Typically, phage surviving selection are subjected to alternate cycles of amplification and selection by the same assay to increase the degree of enrichment for phage bearing dimerizing peptides. Amplification is achieved by reinfection of host cells following selection. Optionally, the stringency of selection can be increased in successive rounds. Optionally, peptides encoded by phage surviving one round of selection can serve as kernel sequences for further mutagenesis. For example, in some methods, the nucleic acid encoding an isolated peptide is mutagenized such that at least one and sometimes, 10, 20, 33 or 50% of the amino acids are varied, and phage encoding the variant peptides are used as the starting materials in a subsequent round of selection. Eventually, clonal isolates of phage surviving selection are picked. The segment of such phage genomes encoding the peptide moiety is sequenced to reveal the identity of the dimerizing peptide.

Dimerizing peptides selected by phage display are useful for mediating multimerization of zinc finger proteins or other types of protein. A typical application of such peptides is to mediate association of two different zinc finger proteins that have proximate target segments within a target sequence. For example, each of the two zinc finger proteins can be a three finger protein with affinity for a 9 base target segment, and the respective target segments can be adjacent or within about 10 or preferably 5 nucleotides of each other in a target sequence. Expression constructs are designed to express the two proteins linked to first and second dimerizing peptide sequences. In some applications, the dimerizing peptides are linked to opposite ends of the two zinc finger proteins so that the peptides are proximate to each other when the two zinc fingers are bound to their respective target segments. For example, if a first zinc finger protein and a second zinc finger protein make their primary contacts with the same strand, and the first zinc finger protein binds 5' relative to a second zinc finger protein on this strand, then typically a peptide is linked to the N terminus of the first zinc protein and the C terminus of the second zinc protein. Alternatively, first and second zinc finger proteins can be designed to bind to target segments on opposite strands of a double stranded target segment. In this situation, dimerizing peptides are included at the same terminus (either N or C) of the first and second zinc finger proteins.

Each of the expressed first and second zinc finger proteins linked to a dimerizing peptide can then bind to its target segment. The two proteins can also bind to each other via the dimerizing peptides. Such binding can occur before or after the two proteins bind to their respective target segments. Associating the two proteins through the dimerizing peptides results in cooperative binding of the two proteins to their proximate target segments, thereby increasing the affinity and/or specificity of binding relative to the independent binding of the zinc finger proteins to their respective target segments.

Zinc finger proteins linked to dimerizing peptides can be used in methods of regulating and detecting target sequences as described in more detail below. The binding specificity of linked zinc fingers is the aggregate of that of the component fingers. Linkage of two zinc finger proteins is advantageous for conferring a unique binding specificity within a mammalian genome. A typical mammalian diploid genome consists of $3 \times 10^9$ bp. Assuming that the four nucleotides A, C, G, and T are randomly distributed, a given 9 bp sequence is present ~23,000 times. Thus, a ZFP recognizing a 9 bp target with absolute specificity would have the potential to bind to ~23,000 sites within the genome. An 18 bp sequence is present once in $3.4 \times 10^{10}$ bp, or about once in a random DNA sequence whose complexity is ten times that of a mammalian genome.

Different zinc finger proteins can be used preassociated or can be used separately in which case they associated in situ. Often zinc finger proteins linked to dimerizing peptides of the invention remain dissociated in solution, and dimerized only on binding to DNA. Such is advantageous in promoting dimerization between two different zinc finger proteins linked to the dimerizing peptides relative to homodimerization of the two copies of the same zinc finger protein. For example, if a target sequence contains adjacent sites for two different zinc finger proteins, both zinc finger proteins can bind simultaneously to the target sequence, and then dimerize with each other mediated by the linked dimerizing peptide. By contrast, two copies of the same zinc finger cannot usually bind adjacent to each other on the same target sequence (unless by coincidence the target contains an inverted repeat of the target site for that zinc finger). Accordingly, multiple copies of the same zinc finger do not typically homodimerize with each other unless the target is designed or selected specifically so that such dimerization should occur. For in vivo applications, zinc finger proteins and linked dimerizing peptides are typically administered indirectly by contacting cells or organisms with an expression vector encoding one or more zinc finger proteins and linked dimerizing peptides. The expression vector is introduced into the cell and expresses the one or more zinc finger proteins and linked dimerizing peptides within the cell. For in vitro applications, such as diagnostics, associated zinc finger proteins are typically used directly in the protein form. In both in vivo and in vitro applications, use of nonnaturally occurring peptides to mediate dimerization offers the advantage relative to natural dimerizing peptides, such as fos and jun, in that nonnatural peptides are unlikely to crossreact with natural proteins within a cell.

II. Zinc Finger Proteins

Zinc finger proteins are formed from zinc finger components. For example, zinc finger proteins can have one to thirty-seven fingers, commonly having 2, 3, 4, 5 or 6 fingers. A zinc finger protein recognizes and binds to a target site (sometimes referred to as a target segment) that represents a relatively small subsequence within a target gene. Each component finger of a zinc finger protein can bind to a subsite within the target site. The subsite includes a triplet of three contiguous bases all on the same strand (sometimes referred to as the target strand). The subsite may or may not also include a fourth base on the opposite strand that is the complement of the base immediately 3' of the three contiguous bases on the target strand (see FIG. 1). In many zinc finger proteins, a zinc finger binds to its triplet subsite substantially independently of other fingers in the same zinc finger protein. Accordingly, the binding specificity of zinc finger protein containing multiple fingers is usually approximately the aggregate of the specificities of its component fingers. For example, if a zinc finger protein is formed from first, second and third fingers that individually bind to triplets XXX, YYY, and ZZZ, the binding specificity of the zinc finger protein is 3'XXX YYY ZZZ5'.

The relative order of fingers in a zinc finger protein from N-terminal to C-terminal determines the relative order of triplets in the 3' to 5' direction in the target. For example, if a zinc finger protein comprises from N-terminal to C-terminal the first, second and third fingers mentioned above, then the zinc finger protein binds to the target segment 3'XXX-YYYZZZ5'. If the zinc finger protein comprises the fingers in another order, for example, second finger, first finger, third finger, then the zinc finger protein binds to a target segment comprising a different permutation of triplets, in this example, 3'YYYXXXZZZ5' (see Berg & Shi, *Science* 271, 1081-1086 (1996)). The assessment of binding properties of a zinc finger protein as the aggregate of its component fingers is, however, only approximate, due to context-dependent interactions of multiple fingers binding in the same protein.

Two or more zinc finger proteins can be linked either covalently or by dimerization to have a target specificity that is the aggregate of that of the component zinc finger proteins (see e.g., Kim & Pabo, *PNAS* 95, 2812-2817 (1998)). For example, a first zinc finger protein having first, second and third component fingers that respectively bind to XXX, YYY and ZZZ can be linked to a second zinc finger protein having first, second and third component fingers with binding specificities, AAA, BBB and CCC. The binding specificity of the combined first and second proteins is thus 3'XXXYYYZZ-Z_AAABBBCCC5', where the underline indicates a short intervening region (typically 0-5 bases of any type). In this situation, the target site can be viewed as comprising two target segments separated by an intervening segment. Linkage by dimerizing peptides has been discussed above. Covalent linkage can be accomplished using any of the following peptide linkers.

T G E K P: (SEQ ID NO:3) (Liu et al., 1997, supra.); (G4S)n (SEQ ID NO:4) (Kim et al., *PNAS* 93, 1156-1160 (1996.); GGRRGGGS (SEQ ID NO:5); LRQRDGERP (SEQ ID NO:6); LRQKDGGGSERP (SEQ ID NO:7); LRQKD (G3S)2 ERP (SEQ ID NO:8). Alternatively, flexible linkers can be rationally designed using computer program capable of modeling both DNA-binding sites and the peptides themselves or by phage display methods. In a further variation, noncovalent linkage can be achieved by fusing two zinc finger proteins with domains promoting heterodimer formation of the two zinc finger proteins. For example, one zinc finger protein can be fused with fos and the other with jun (see Barbas et al., WO 95/119431).

A component finger of zinc finger protein typically contains about 30 amino acids and has the following motif (N-C) (SEQ ID NO:1):

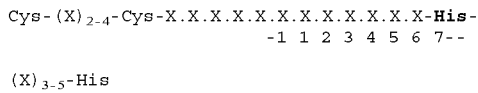

(X)$_{3-5}$-His

The two invariant histidine residues and two invariant cysteine residues in a single beta turn are co-ordinated through zinc (see, e.g., Berg & Shi, *Science* 271, 1081-1085 (1996)). The above motif shows a numbering convention that is standard in the field for the region of a zinc finger conferring binding specificity. The amino acid on the left (N-terminal side) of the first invariant His residues is assigned the number +6, and other amino acids further to the left are assigned successively decreasing numbers. The alpha helix begins at residue 1 and extends to the residue following the second conserved histidine. The entire helix is therefore of variable length, between 11 and 13 residues. The process of designing or selecting a nonnaturally occurring or variant ZFP typically starts with a natural ZFP as a source of framework residues. The process of design or selection serves to define nonconserved positions (i.e., positions −1 to +6) so as to confer a desired binding specificity. One suitable ZFP is the DNA binding domain of the mouse transcription factor Zif268. The DNA binding domain of this protein has the amino acid sequence:

YACPVESCDRRFSRSDELTRHIRIHTGQKP (F1) (SEQ ID NO:9)

FQCRICMRNFSRSDHLTTHIRTHTGEKP (F2) (SEQ ID NO:10)

FACDICGRKFARSDERKRHTKIHLRQK (F3) (SEQ ID NO:11)

and binds to a target 5' GCG TGG GCG 3'.

Another suitable natural zinc finger protein as a source of framework residues is Sp-1. The Sp-1 sequence used for construction of zinc finger proteins corresponds to amino acids 531 to 624 in the Sp-1 transcription factor. This sequence is 94 amino acids in length. The amino acid sequence of Sp-1 is as follows PGKKKQHICHIQGCGKVYGKTSHLRAHL-RWHTGERP
FMCTWSYCGKRFTRSDELQRHKRTHTGEKK
FACPECPKRFMRSDHLSKHIKTHQNKKG (SEQ ID NO:12)

Sp-1 binds to a target site 5'GGG GCG GGG3'.

An alternate form of Sp-1, an Sp-1 consensus sequence, has the following amino acid sequence:

meklrngsgd
PGKKKQHACPECGKSFSKSSHLRAHQRTHTGERP
YKCPECGKSFSRSDELQRHQRTHTGEKP
YKCPECGKSFSRSDHLSKHQRTHQNKKG (SEQ ID NO:13) (lower case letters are a leader sequence from Shi & Berg, *Chemistry and Biology* 1, 83-89. (1995). The optimal binding sequence for the Sp-1 consensus sequence is 5'GGGGCGGGG3'. Other suitable ZFPs are described below.

There are a number of substitution rules that assist rational design of some zinc finger proteins (see Desjarlais & Berg, *PNAS* 90, 2256-2260 (1993); Choo & Klug, *PNAS* 91, 11163-11167 (1994); Desjarlais & Berg, *PNAS* 89, 7345-7349 (1992); Jamieson et al., supra; Choo et al., WO 98/53057, WO 98/53058; WO 98/53059; WO 98/53060). Many of these rules are supported by site-directed mutagenesis of the three-finger domain of the ubiquitous transcription factor, Sp-1 (Desjarlais and Berg, 1992; 1993) One of these rules is that a 5' G in a DNA triplet can be bound by a zinc finger incorporating arginine at position 6 of the recognition helix. Another substitution rule is that a G in the middle of a subsite can be recognized by including a histidine residue at position 3 of a zinc finger. A further substitution rule is that asparagine can be incorporated to recognize A in the middle of triplet, aspartic acid, glutamic acid, serine or threonine can be incorporated to recognize C in the middle of triplet, and amino acids with small side chains such as alanine can be incorporated to recognize T in the middle of triplet. A further substitution rule is that the 3' base of triplet subsite can be recognized by incorporating the following amino acids at position −1 of the recognition helix: arginine to recognize G, glutamine to recognize A, glutamic acid (or aspartic acid) to recognize C, and threonine to recognize T. Although these substitution rules are useful in designing zinc finger proteins they do not take into account all possible target sites. Furthermore, the assumption underlying the rules, namely that a particular amino acid in a zinc finger is responsible for binding to a particular base in a subsite is only approximate. Context-dependent interactions between proximate amino acids in a finger or binding of multiple amino acids to a single base or vice versa can cause variation of the binding specificities predicted by the existing substitution rules.

Zinc finger proteins are often expressed with a heterologous domain as fusion proteins. Common domains for addition to the ZFP include, e.g., transcription factor domains (activators, repressors, co-activators, co-repressors), silencers, oncogenes (e.g., myc, jun, fos, myb, max, mad, rel, ets, bcl, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. A preferred domain for fusing with a ZFP when the ZFP is to be used for repressing expression of a target gene is a the KRAB repression domain from the human KOX-1 protein (Thiesen et al., *New Biologist* 2, 363-374 (1990); Margolin et al., *Proc. Natl. Acad. Sci. USA* 91, 4509-4513 (1994); Pengue et al., *Nucl. Acids Res.* 22:2908-2914 (1994); Witzgall et al., *Proc. Natl. Acad. Sci. USA* 91, 4514-4518 (1994). Preferred domains for achieving activation include the HSV VP16 activation domain (see, e.g., Hagmann et al., *J. Virol.* 71, 5952-5962 (1997)) nuclear hormone receptors (see, e.g., Torchia et al., *Curr. Opin. Cell. Biol.* 10:373-383 (1998)); the p65 subunit of nuclear factor kappa B (Bitko & Barik, *J. Virol.* 72:5610-5618 (1998) and Doyle & Hunt, *Neuroreport* 8:2937-2942 (1997)); Liu et al., *Cancer Gene Ther.* 5:3-28 (1998)), or artificial chimeric functional domains such as VP64 (Seifpal et al., *EMBO J.* 11, 4961-4968 (1992)).

An important factor in the administration of polypeptide compounds, such as the ZFPs, is ensuring that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as ZFPs across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, *Current Opinion in Neurobiology* 6:629-634 (1996)). Another subsequence, the h (hydrophobic) domain of signal peptides, was found to have similar cell membrane translocation characteristics (see, e.g., Lin et al., *J. Biol. Chem.* 270:1 4255-14258 (1995)).

Examples of peptide sequences which can be linked to a ZFP of the invention, for facilitating uptake of ZFP into cells, include, but are not limited to: an 11 animo acid peptide of the tat protein of HIV; a 20 residue peptide sequence which corresponds to amino acids 84-103 of the p16 protein (see Fahraeus et al., *Current Biology* 6:84 (1996)); the third helix of the 60-amino acid long homeodomain of Antennapedia (Derossi et al., *J. Biol. Chem.* 269:10444 (1994)); the h region of a signal peptide such as the Kaposi fibroblast growth factor (K-FGF) h region (Lin et al., supra); or the VP22 translocation domain from HSV (Elliot & O'Hare, *Cell* 88:223-233 (1997)). Other suitable chemical moieties that provide enhanced cellular uptake may also be chemically linked to ZFPs.

Toxin molecules also have the ability to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al., *J. Biol. Chem.*, 268:3334-3341 (1993); Perelle et al., *Infect. Immun.*, 61:5147-5156 (1993); Stenmark et al., *J. Cell Biol.* 113:1025-1032 (1991); Donnelly et al., *PNAS* 90:3530-3534 (1993); Carbonetti et al., *Abstr. Annu. Meet. Am. Soc. Microbiol.* 95:295 (1995); Sebo et al., *Infect. Immun.* 63:3851-3857 (1995); Klimpel et al., *PNAS U.S.A.* 89:10277-10281 (1992); and Novak et al., *J. Biol. Chem.* 267:17186-17193 1992)).

Such subsequences can be used to translocate ZFPs across a cell membrane. ZFPs can be conveniently fused to or derivatized with such sequences. Typically, the translocation sequence is provided as part of a fusion protein. Optionally, a linker can be used to link the ZFP and the translocation sequence. Any suitable linker can be used, e.g., a peptide linker.

III. Phage Display Method

The technique of phage display has provided a largely empirical means of generating zinc finger proteins with a desired target specificity (see e.g., Rebar, U.S. Pat. No. 5,789, 538; Choo et al., WO 96/06166; Barbas et al., WO 95/19431 and WO 98/543111; Jamieson et al., supra). The method can be used in conjunction with, or as an alternative to rational design.

In the present invention, phage display is used for selection of linkers. The method involves the generation of diverse libraries of peptides, typically linked to the same zinc finger protein, followed by affinity selection for phage bearing peptides with dimerizing activity. To use this method, the experimenter typically proceeds as follows. First, a gene for a zinc finger protein binding a known target segment is selected. A target sequence is then designed bearing two copies of the target segment in opposing orientations. The two copies can be immediately adjacent or separated by up to about 5 nucleotides. Next, a library of nucleic acid segments encoding potential dimerizing peptides is provided. This library can be a completely random peptide library, or can represent variants of a known sequence or can include a number of known peptide sequences. A phage or phagemid expression vector is then engineered to encode a fusion protein comprising an outersurface phage coat protein or fragment thereof, a potential dimerizing peptide, and the zinc finger protein. The potential dimerizing peptide varies between different library members whereas the zinc finger protein is the same. The dimerizing peptide and zinc finger protein can be linked in either order to the phage coat protein. Typically, the phage coat protein is pIII of a filamentous phage. The zinc finger gene and segment encoding the potential dimerizing peptide are inserted between segments of gene III encoding the membrane export signal peptide and the remainder of pIII, so that the zinc finger protein is expressed as an amino-terminal fusion with pIII or in the mature, processed protein. When using phagemid vectors, the zinc finger gene and potential dimerizing peptide can also be fused to a truncated version of gene III encoding, minimally, the C-terminal region required for assembly of pIII into the phage particle. The resultant vector library is transformed into *E. coli* and used to produce filamentous phage which express variant peptides linked to a constant zinc finger protein on their surface as fusions with the coat protein pIII. If a phagemid vector is used, then the this step requires superinfection with helper phage. The phage library is then incubated with target DNA sequence, and affinity selection methods are used to isolate phage which bind target with high affinity from bulk phage. Typically, the DNA target is immobilized on a solid support, which is then washed under conditions sufficient to remove all but the tightest binding phage. After washing, any phage remaining on the support are recovered via elution under conditions which disrupt zinc finger—DNA binding. Recovered phage are used to infect fresh *E. coli*., which is then amplified and used to produce a new batch of phage particles. Selection and amplification are then repeated as many times as is necessary to enrich the phage pool for tight binders such that these may be identified using sequencing and/or screening methods. Although the method is illustrated for pIII fusions, analogous principles can be used to screen ZFP variants as pVIII fusions.

Eukaryotic viruses can be used to display polypeptides in an analogous manner. For example, display of human heregulin fused to gp70 of Moloney murine leukemia virus has been reported by Han, et al., *Proc. Natl. Acad. Sci. USA* 92:9747-9751 (1995). Spores can also be used as replicable genetic packages. In this case, polypeptides are displayed from the outer surface of the spore. For example, spores from *B. subtilis* have been reported to be suitable. Sequences of coat proteins of these spores are provided by Donovan, et al., *J. Mol. Biol.* 196:1-10 (1987). Eucaryotic or bacterial cells can also be used as replicable genetic packages. Polypeptides to be displayed are inserted into a gene encoding a cell protein that is expressed on the cells surface. Yeast and bacterial cells including *Salmonella typhimurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis,* and especially *Escherichia coli* are preferred. Details of outer surface proteins are discussed by Ladner, et al., U.S. Pat. No. 5,571,698, and Georgiou, et al., *Nature Biotechnology* 15:29-34 (1997) and references cited therein. For example, the lamB protein of *E. coli* is suitable.

IV. Selection of Target Gene

Zinc finger proteins can be used to modulate the expression of any target polynucleotide sequence. The sequence can be for example, genomic, cDNA or RNA or an expressed sequence tag (EST). Typically, the target polynucleotide includes a gene or a fragment thereof. The term gene is used broadly to include, for example, exonic regions, intronic regions, 5'UTRs, 3'UTRs, 5' flanking sequences, 3' flanking sequences, promoters, enhancers, transcription start sites, ribosome binding sites, regulatory sites, poly-adenylation sites. Target genes can be cellular, viral or from other sources including purely theoretical sequences. Target gene sequences can be obtained from databases, such as GenBank, the published literature or can be obtained de novo. Target genes include genes from pathological viruses and microorganisms for which repression of expression can be used to abort infection. Examples of pathogenic viruses include hepatitis (A, B, or C), herpes virus (e.g., VZV, HSV-1, HSV-6, HSV-II, and CMV, Epstein Barr virus), HIV, ebola, adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus. Some examples of pathogenic bacteria include chlamydia, rickettsial bacteria, mycobacteria, staphylococci, treptocci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme disease bacteria.

Target genes also include genes from human or other mammals that contribute to disease. Some such genes are oncogenes, tumor suppressors or growth factors that contribute to cancer. Examples of oncogenes include hMSH2 (Fishel et al., *Cell* 75, 1027-1038 (1993)) and hMLH1 (Papadopoulos et al., *Science* 263, 1625-1628 (1994)). Some examples of growth factors include fibroblast growth factor, platelet-derived growth factor, GM-SCF, VEGF, EPO, Erb-B2, and hGH. Other human genes contribute to disease by rendering a subject susceptible to infection by a microorganism or virus. For example, certain alleles of the gene encoding the CCR5 receptor render a subject susceptible to infection by HIV. Other human genes, such as that encoding amyloid precursor protein or ApoE, contribute to other diseases, such as Alzheimer's disease.

Target genes also include genes of human or other mammals that provide defense mechanisms against diseases due to other sources. For example, tumor repressor genes, provide protection against cancer. Expression of such genes is desirable and zinc finger proteins are used to activate expression.

Target genes also include genes that are normally turned off or expressed at low levels but which through activation can be used to substitute for another defective gene present in some individuals. For example, the fetal hemaglobin genes, which are normally inactive in adult humans, can be activated to substitute for the defective beta-globin gene in individuals with sickle cell anemia.

Target genes also include plant genes for which repression or activation leads to an improvement in plant characteristics, such as improved crop production, disease or herbicide resistance. For example, repression of expression of the FAD2-1 gene results in an advantageous increase in oleic acid and decrease in linoleic and linoleic acids.

Once a target gene has been determined, target segments within the gene are selected which are to be bound by zinc finger proteins. Typically, two target segments are selected within the same gene to be bound by two zinc finger proteins to be associated by dimerizing peptides. Typically, the two segments are each of 9 or 10 bases and are adjacent or within about 5 nucleotides of each. Criteria for selecting target segments are described in 09/229,007 filed Jan. 12, 1999 (incorporated by reference in its entirety for all purposes).

V. Production of ZFPs and Dimerizing Peptides

ZFP polypeptides, dimerizing peptides linked to the same, and nucleic acids encoding fusion proteins of ZFPs and dimerizing peptides can be made using routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)). In addition, nucleic acids less than about 100 bases can be custom ordered from any of a variety of commercial sources, such as The Midland Certified Reagent Company (mcrc@oligos.com), The Great American Gene Company, ExpressGen Inc., Operon Technologies Inc. (Alameda, Calif.). Similarly, peptides can be custom ordered from any of a variety of sources, such as PeptidoGenic (pkim@ccnet.com), HTI Bio-products, inc., BMA Biomedicals Ltd (U.K.), Bio.Synthesis, Inc.

Oligonucleotides can be chemically synthesized according to the solid phase phosphoramidite triester method first described by Beaucage & Caruthers, *Tetrahedron Letts.* 22:1859-1862 (1981), using an automated synthesizer, as described in Van Devanter et al., *Nucleic Acids Res.* 12:6159-6168 (1984). Purification of oligonucleotides is by either denaturing polyacrylamide gel electrophoresis or by reverse phase HPLC. The sequence of the cloned genes and synthetic oligonucleotides can be verified after cloning using, e.g., the chain termination method for sequencing double-stranded templates of Wallace et al., *Gene* 16:21-26 (1981).

Figure 2:
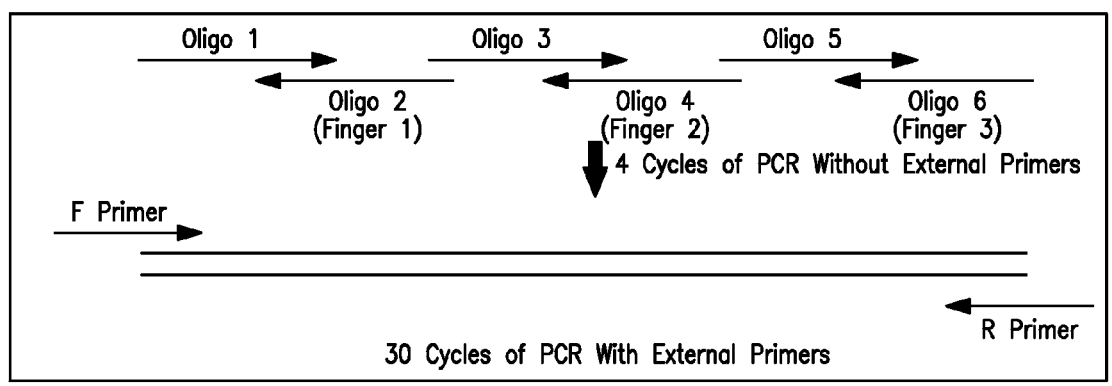
FIG. 2 shows the process of assembling a nucleic acid encoding a designed ZFP.

Two alternative methods are typically used to create the coding sequences required to express DNA-binding peptides. One protocol is a PCR-based assembly procedure that utilizes six overlapping oligonucleotides (FIG. 2). Three oligonucleotides (oligos 1, 3, and 5 in FIG. 2) correspond to "universal" sequences that encode portions of the DNA-binding domain between the recognition helices. These oligonucleotides typically remain constant for all zinc finger constructs. The other three "specific" oligonucleotides (oligos 2, 4, and 6 in FIG. 2) are designed to encode the recognition helices. These oligonucleotides contain substitutions primarily at positions −1, 2, 3 and 6 on the recognition helices making them specific for each of the different DNA-binding domains.

The PCR synthesis is carried out in two steps. First, a double stranded DNA template is created by combining the six oligonucleotides (three universal, three specific) in a four cycle PCR reaction with a low temperature annealing step, thereby annealing the oligonucleotides to form a DNA "scaffold." The gaps in the scaffold are filled in by high-fidelity thermostable polymerase, the combination of Taq and Pfu polymerases also suffices. In the second phase of construction, the zinc finger template is amplified by external primers designed to incorporate restriction sites at either end for cloning into a shuttle vector or directly into an expression vector.

An alternative method of cloning a DNA-binding protein relies on annealing complementary oligonucleotides encoding the specific regions of the desired ZFP. This particular application requires that the oligonucleotides be phosphorylated prior to the final ligation step. This is usually performed before setting up the annealing reactions. In brief, the "universal" oligonucleotides encoding the constant regions of the proteins (oligos 1, 2 and 3 of above) are annealed with their complementary oligonucleotides. Additionally, the "specific" oligonucleotides encoding the finger recognition helices are annealed with their respective complementary oligonucleotides. These complementary oligos are designed to fill in the region that was previously filled in by polymerase in the above-mentioned protocol. The complementary oligos to the common oligos 1 and finger 3 are engineered to leave overhanging sequences specific for the restriction sites used in cloning into the vector of choice in the following step. The second assembly protocol differs from the initial protocol in the following aspects: the "scaffold" encoding the newly designed ZFP is composed entirely of synthetic DNA thereby eliminating the polymerase fill-in step, additionally the fragment to be cloned into the vector does not require amplification. Lastly, the design of leaving sequence-specific overhangs eliminates the need for restriction enzyme digests of the inserting fragment. Alternatively, changes to ZFP recognition helices can be created using conventional site-directed mutagenesis methods.

Both assembly methods require that the resulting fragment encoding the newly designed ZFP be ligated into a vector. Ultimately, the ZFP-encoding sequence is cloned into an expression vector. Optionally, a nucleic acid segment encoding a dimerizing peptide can be cloned into the vector so as to be expressed in frame with the ZFP. Expression vectors that are commonly utilized include a modified pMAL-c2 bacterial expression vector (New England BioLabs or an eukaryotic expression vector, pcDNA (Promega). The final constructs are verified by sequence analysis.

Any suitable method of protein purification can be used to purify ZFPs of the invention (see, Ausubel, supra, Sambrook, supra). In addition, any suitable host can be used for expression, e.g., bacterial cells, insect cells, yeast cells, mammalian cells, and the like.

Expression of a zinc finger protein, and optionally, a dimerizing peptide linker, fused to a maltose binding protein (MBP-ZFP) in bacterial strain JM109 allows for straightforward purification through an amylose column (NEB). High expression levels of the zinc finger chimeric protein can be obtained by induction with IPTG since the MBP-ZFP fusion in the pMal-c2 expression plasmid is under the control of the tac promoter (NEB). Bacteria containing the MBP-ZFP fusion plasmids are inoculated in to 2×YT medium containing 10 μM ZnCl2, 0.02% glucose, plus 50 μg/ml ampicillin and shaken at 37° C. At mid-exponential growth IPTG is added to 0.3 mM and the cultures are allowed to shake. After 3 hours the bacteria are harvested by centrifugation, disrupted by sonication or by passage through a french pressure cell or through the use of lysozyme, and insoluble material is removed by centrifugation. The MBP-ZFP proteins are captured on an amylose-bound resin, washed extensively with buffer containing 20 mM Tris-HCl (pH 7.5), 200 mM NaCl, 5 mM DTT and 50 μM ZnCl2, then eluted with maltose in essentially the same buffer (purification is based on a standard protocol from NEB). Purified proteins are quantitated and stored for biochemical analysis.

The dissociation constants of the purified proteins, e.g., Kd, are typically characterized via electrophoretic mobility shift assays (EMSA) (Buratowski & Chodosh, in *Current Protocols in Molecular Biology* pp. 12.2.1-12.2.7 (Ausubel ed., 1996)). Affinity is measured by titrating purified protein against a fixed amount of labeled double-stranded oligonucleotide target. The target typically comprises the natural binding site sequence flanked by the 3 bp found in the natural sequence and additional, constant flanking sequences. The natural binding site is typically 9 bp for a three-finger protein and 2×9 bp+intervening bases for a six finger ZFP. The annealed oligonucleotide targets possess a 1 base 5' overhang that allows for efficient labeling of the target with T4 phage polynucleotide kinase. For the assay the target is added at a concentration of 1 nM or lower (the actual concentration is kept at least 10-fold lower than the than the expected dissociation constant), purified ZFPs are added at various concentrations, and the reaction is allowed to equilibrate for at least 45 min. In addition the reaction mixture also contains 10 mM Tris (pH 7.5), 100 mM KCl, 1 mM MgCl2, 0.1 mM ZnCl2, 5 mM DTT, 10% glycerol, 0.02% BSA. (NB: in earlier assays poly d(IC) was also added at 10-100 μg/μl.)

The equilibrated reactions are loaded onto a 10% polyacrylamide gel, which has been pre-run for 45 min in Tris/glycine buffer, then bound and unbound labeled target is resolved by electrophoresis at 150 V. (alternatively, 10-20% gradient Tris-HCl gels, containing a 4% polyacrylamide stacker, can be used) The dried gels are visualized by autoradiography or phosphorimaging and the apparent Kd is determined by calculating the protein concentration that gives half-maximal binding.

The assays can also include determining active fractions in the protein preparations. Active fractions are determined by stoichiometric gel shifts where proteins are titrated against a high concentration of target DNA. Titrations are done at 100, 50, and 25% of target (usually at micromolar levels).

VI. Applications of ZFPs

ZPFs that bind to a particular target gene, and the nucleic acids encoding them, can be used for a variety of applications. These applications include therapeutic methods in which a ZFP or a nucleic acid encoding it is administered to a subject and used to modulate the expression of a target gene within the subject (see copending application Ser. No. 09/229,037 filed Jan. 12, 1999). The modulation can be in the form of repression, for example, when the target gene resides in a pathological infecting microorganisms, or in an endogenous gene of the patient, such as an oncogene or viral receptor, that is contributing to a disease state. Alternatively, the modulation can be in the form of activation when activation of expression or increased expression of an endogenous cellular gene can ameliorate a diseased state. For such applications, ZFPs, or more typically, nucleic acids encoding them are formulated with a pharmaceutically acceptable carrier as a pharmaceutical composition.

Pharmaceutically acceptable carriers are determined in part by the particular composition being administered, as well as by the particular method used to administer the composition. (see, e.g., Remington's Pharmaceutical Sciences, 17$^{th}$ ed. 1985)). The ZFPs, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like. Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

The dose administered to a patient should be sufficient to effect a beneficial therapeutic response in the patient over time. The dose is determined by the efficacy and $K_d$ of the particular ZFP employed, the target cell, and the condition of the patient, as well as the body weight or surface area of the patient to be treated. The size of the dose also is determined by the existence, nature, and extent of any adverse side-effects that accompany the administration of a particular compound or vector in a particular patient In other applications, ZFPs are used in diagnostic methods for sequence specific detection of target nucleic acid in a sample. For example, ZFPs can be used to detect variant alleles associated with a disease or phenotype in patient samples. As an example, ZFPs can be used to detect the presence of particular mRNA species or cDNA in a complex mixtures of mRNAs or cDNAs. As a further example, ZFPs can be used to quantify copy number of a gene in a sample. For example, detection of loss of one copy of a p53 gene in a clinical sample is an indicator of susceptibility to cancer. In a further example, ZFPs are used to detect the presence of pathological microorganisms in clinical samples. This is achieved by using one or more ZFPs specific to genes within the microorganism to be detected. A suitable format for performing diagnostic assays employs ZFPs linked to a domain that allows immobilization of the ZFP on an ELISA plate. The immobilized ZFP is contacted with a sample suspected of containing a target nucleic acid under conditions in which binding can occur. Typically, nucleic acids in the sample are labeled (e.g., in the course of PCR amplification). Alternatively, unlabelled probes can be detected using a second labelled probe. After washing, bound-labelled nucleic acids are detected.

ZFPs also can be used for assays to determine the phenotype and function of gene expression. Current methodologies for determination of gene function rely primarily upon either overexpression or removing (knocking out completely) the gene of interest from its natural biological setting and observing the effects. The phenotypic effects observed indicate the role of the gene in the biological system.

One advantage of ZFP-mediated regulation of a gene relative to conventional knockout analysis is that expression of the ZFP can be placed under small molecule control. By controlling expression levels of the ZFPs, one can in turn control the expression levels of a gene regulated by the ZFP to determine what degree of repression or stimulation of expression is required to achieve a given phenotypic or biochemical effect. This approach has particular value for drug development. By putting the ZFP under small molecule control, problems of embryonic lethality and developmental compensation can be avoided by switching on the ZFP repressor at a later stage in mouse development and observing the effects in the adult animal. Transgenic mice having target genes regulated by a ZFP can be produced by integration of the nucleic acid encoding the ZFP at any site in trans to the target gene. Accordingly, homologous recombination is not required for integration of the nucleic acid. Further, because the ZFP is trans-dominant, only one chromosomal copy is needed and therefore functional knock-out animals can be produced without backcrossing. Although the foregoing invention has been described in detail for purposes of clarity of understanding, it will be obvious that certain modifications may be practiced within the scope of the appended claims. All publications and patent documents cited herein are hereby incorporated by reference in their entirety for all purposes to the same extent as if each were so individually denoted.

Example 1

Dimerization of Zinc Fingers Mediated by Peptides Evolved in Vitro from Random Sequences Peptides that mediate dimerization of attached zinc finger DNA-binding domains have been evolved in vitro starting from random sequences. We first used phage display to select dimerization elements from libraries of random 15-residue polypeptides that were fused to the N terminus of the zinc finger domains. We then reoptimized these peptides by sequentially randomizing five-residue blocks (proceeding across the peptide in three steps) and selecting variant peptides that further stabilized the protein-DNA complex. Biochemical experiments confirmed that the selected peptides promote dimerization of the zinc fingers on an appropriate DNA target site. These results demonstrate that dimerization units can be obtained readily from random polypeptide libraries of moderate complexity. Our success reemphasizes the utility of searching random peptide libraries in protein design projects, and the sequences presented here may be useful when designing novel transcription factors.

The affinity and specificity of DNA-binding proteins depend not only on interactions with the DNA but also on interactions with proteins that bind at neighboring sites. Such protein-protein interactions may involve homo- or heterodimerization or the assembly of multiprotein complexes. Dimerization strategies already have been tested, in structure-based design efforts, to create DNA-binding proteins with enhanced affinity and specificity. In the first such study (1), computer modeling was used to design a fusion between zinc finger subdomains from Zif268 and the dimerization element from Gal4. Recent design efforts with zinc fingers also have used leucine zipper dimerization motifs in an analogous manner.

The selection of dimerization elements from libraries of random peptides represents an intriguing alternative to structure-based design and raises many interesting questions. How common are functional dimerization units? Do the selected structures always resemble known motifs? Can we obtain new dimerization units that would be useful when designing transcription factors for potential applications in gene therapy?

Phage display (reviewed in refs. 2 and 3) provides a powerful method for selecting functional peptides from large populations of random polypeptides. Peptide libraries displayed on phage often have been screened for peptide-protein interactions in studies that focus on epitope mapping, analysis of substrate specificity, and the development of leads for drug design. Peptides that can substitute for larger protein domains also have been generated, either through stepwise minimization and reoptimization of a naturally occurring domain or by selection from random sequence libraries (reviewed in ref. 4). In one study, a peptide selected to bind the erythropoietin receptor (5) was found to induce dimerization of the receptor-peptide complex (6), demonstrating that self-associating peptides can—at least under some circumstances—be isolated from random polypeptide sequences.

In this study, we used phage display to select and optimize peptides that mediate dimerization of DNA-binding modules. Our work may have practical implications in the design of DNA-binding proteins and, more generally, demonstrates how random peptide extensions provide a basis for selecting proteins with desired functions. These results also may have implications regarding the role of protein-protein interactions in the evolution of transcription factors.

Materials and Methods

Phage Display Libraries. Phagemid vectors used in the selections were created from pZif12 (7) by restoring the reading frame between the Zif12-coding region and gene III and by introducing convenient restriction sites at the start of Zif12. Libraries containing randomized peptides were constructed by cassette mutagenesis, using NN(G/C/T) randomized condons for the initial libraries and NN(G/T) for the reoptimization libraries. The complete fusion protein used for phage display contained a PelB signal sequence; a short leader peptide ($NH_2$-EPRAQNS in initial selections and $NH_2$-EP in reoptimizations); the random peptide; residues 4-60 of Zif268 (numbering as in ref. 8); a linker that includes an amber condom; and residues 23-424 of M13 gene III product. The ligated phagemid libraries were electroporated into XL-1 Blue E. coli cells, yielding ≈$10^8$ transformants for the initial selection libraries and ≈$10^9$ transformants for each of the reoptimization libraries.

Phage Selections. For the initial selections, phage were grown, harvested, and processed essentially as described previously for zinc finger phagemid selections (7). Selections during the block-reoptimization steps were conducted similarly, but with the following set of changes. binding reactions included 2 mMDTT to minimize the risk of selecting disulfide bonded dimer interfaces. Phage-DNA complexes were captured by streptavidin-coated paramegnetic beads (Dynal, Great Neck, N.Y.) that had been equilibrated in pZif12 wash buffer (7). Five microliters of a 10-mg/ml suspension of beads was used to capture up to 10-mg/ml suspension of beads was used to capture up to 10 pmol of DNA site (with bound phage). The beads were washed (five times using 0.5 ml for each 8-min wash) and treated with high-salt elution buffer (7). To increase stringency, (i) binding, capture, and elution were performed at 37° C. in the second and third reoptimization steps, and (ii) in the third step, the target DNA site contained a mutation in one of the Zif12-binding sites (the half-site distal to the biotin was TGAGCG). The target DNA concentration also was lowered through the course of the reoptimization to help force competition among members of the phage pool and to further increase stringency. In the first block-reoptimization step, the target DNA concentration was reduced from 40 nM (cycles 1-3) to 8 nM (cycles 4-6) and then to 2 nM (cycles 7-9), with the salmon sperm competitor DNA concentration lowered proportionately at each stage. In the second step, concentrations were 20 nM (cycle 1) or 2 nM. In the third step, the mutant DNA was present at 1 nM throughout. In the later stages of each block-reoptimization step, we estimate that the phage concentration was 10- to 20-fold higher than the target DNA.

Protein Production and Purification. DNA fragments encoding peptide-Zif12 fusions with Met-Ala at their N terminus) were cloned into pET-21d (Novagen) and expressed in BL21 (DE3) or BL21(DE3) pLysS cells. Cultures were induced, lysed, and sonicated as recommended (Novagen). Peptides were present in insoluble inclusion bodies and were purified by reversed-phase batch extraction (using Waters Sep pak C18 cartridges) and reversed-phase HPLC as described (8). The Zif12 peptide (amino acids 2-59 of Zif268) and peptide 2 were expressed as glutathione S-transferase (GST) fusion proteins from PGEX-2tT and pGEX-6p-3 (Pharmacia), respectively. These peptides were purified by affinity chromatography and cleaved from the GST as directed (Pharmacia), leaving a Gly-Ser dipeptide at the N terminus of Zif12 and a heptapeptide (GPLGSDP) at the N terminus of peptide 2. The cleaved peptides were purified further by reversed-phase HPLC. All peptides were reconstituted from lyophilized HPLC fractions and refolded as described (9), and their concentrations were quantified by comparison with BSA standards in SDS/PAGE using Coomassie staining. For peptides that gave a stable gel shift (peptides 1*, 3, and 5*), the active concentration of peptide was determined as described (9), and we found that each of these samples was fully active for DNA binding.

DNA-Binding Assays. Gel mobility-shift assays (10) and DNase I footprinting experiments (11) were used to asses the DNA-binding activity of various peptides. Only peptides 1*, 3, and 5* produced complexes that were sufficiently stable for quantitative gel-shift assays, and footprinting was used to measure the affinity of the other peptides.

Labeled DNA probes were generated as follows. For the gel-shift studies oligos corresponding to the phage-selection target site (5'GGTTGCAGTGGGCGCGCCCACAGTACT-TGAACGTAACG-3' and 5'-CGTTACGTTCAAGTACT-GTGGGCGCGCCCACTGC-3', Zif12 sites in bold) or a single-site mutant (bold regions above replaced with the sequences 5'-TGGGCGTATGCT-3' and 5' AGCATACGCCCA-3') were annealed and end-labeled with Klenow. A labeled restriction fragment was used for quantitative studies. The oligos 5'-GGAATTCCTGATCAA-GATCTGGTCACGTCCATAGGCTAGGCAT-GTCAAGGCTGTATG-3' and 5'-GGGATCCACTCGCGAACGCGTCCTTG-TAGTGGGCGCGCCCACATACAGCCTTGACA T-3' (Zif12 sites in bold) were annealed, extended by mutually primed extension, and cloned into the EcoRI and BamHI sites of pBluescript II SK(+). The probe was prepared by digesting the plasmid with EcoRI and NotI; labeling the DNA with Klenow, ($\alpha$-$^{32}$P)dCTP, and ($\alpha$-$^{32}$P)dGTP; and purifying the small fragment by native PAGE.

Binding reactions (typically 10 μl) contained the labeled DNA site (at >100-fold below the protein concentration at half-maximal binding), protein (for quantitative assays, we used 1.3- to 2.0-fold dilution steps over a range of four orders of magnitude), and a buffer containing 15 mM Hepes, pH 7.8, 60 mM potassium acetate, to mM potassium glutamate, 5 mM $MgCl_2$, 20 μM $ZnSO_4$, 5% glycerol, 0.1% Nonidet P-40, 1 mM DTT, and 0.1 mg/ml acetylated BSA. After equilibrating the binding reactions at 4° C. (1.5-16 hr, depending on the peptide), the reactions either were resolved by native PAGE (7.5% 37.5:1 acrylamide/bisacrylamide with 2.5% glycerol, run at 4° C. in electrophoresis buffer containing 25 mM Tris, 190 mM glycine, and 1 mM EDTA) or treated with DNase I. DNase I reactions (4 min, 4° C. using 2.5 µl of 30 µg/ml DNase I for 10 µl reaction) were terminated, prepared, and electrophoresed as described (12). Data were collected by using a PhosphorImager (Molecular Dynamics).

To determine dissociation constants ($K_d$) for the fusion peptides, binding data for the selected peptides were fit by nonlinear regression to the equation $\theta=1/(1+K_d/(P)^2)$, where $\theta$ is the fraction of DNA bound and (P) is the concentration of free protein, which approximately equals the total protein concentration in experiments. This equation describes the binding of two protein molecules to a DNA molecule with strict cooperativity. Data for Zif12, which bound essentially noncooperatively, were fit to the equation $\theta=1/(1+K_{d'}/(P))$, where $K_{d'}$ is the dissociation constant for a Zif12 monomer; the corresponding $K_d$ for the overall reaction of two Zif12 monomer with the DNA was calculated as $(K_{d'})^2$.

Sedimentation Equilibrium. Peptide samples at three concentrations, ranging from ≈10 µM to ≈100 µM, were centrifuged to equilibrium in a Beckman Optima XL-A at 20,000 and 30,000 rpm at 4° C. in a buffer containing 15 mM Tris, pH 7.8, 150 mM KCl, 5 mM $MgCl_2$, 20 µM $ZnSO_4$, and 0.2 mM DTT. Solvent density and partial specific volumes of peptides were calculate at described (13). The sedimentation data were analyzed by methods described in refs. 14 and 15, using the program NONLIN (16).

Results

To select dimerization motifs, we attached random peptides to a DNA-binding domain and selected those fusion proteins that could bind more stably to a symmetric DNA site. Random 15- and 30-residue peptides were expressed at the amino terminus of the first two zinc fingers of Zif268 (8, 17) (we refer to this two-finger peptide as Zif12), and these peptide-Zif12 fusions were displayed on filamentous bacteriophage. Phage from the 15- and 30-mer libraries, representing $10^8$ different sequences from each library, were pooled, and our affinity-selection protocol was used with a target DNA duplex containing an inverted repeat of the Zif12-binding site. The original Zif12 peptide, which lacks any N-terminal extension, binds specifically, but weakly, to the "half-site" sequence TGGGCG, and Zif12 phage are not retained by the target DNA. Therefore, our protocol enriches for phage that display peptides that augment the DNA-binding activity of the zinc fingers.

After seven cycles of selection and amplification, the phage pool bound more than 100-fold more efficiently than the initial random libraries, indicating successful enrichment of higher-affinity phage. We sequenced 45 clones from this final phage pool and found 6 different 15-mer peptide sequences (FIG. 4A). These peptides did not share any obvious homology, aside from a basic residue present at the final position of each sequence. BLAST searches (18) showed no significant similarity between the selected peptides and known natural proteins.

Figure 4B:
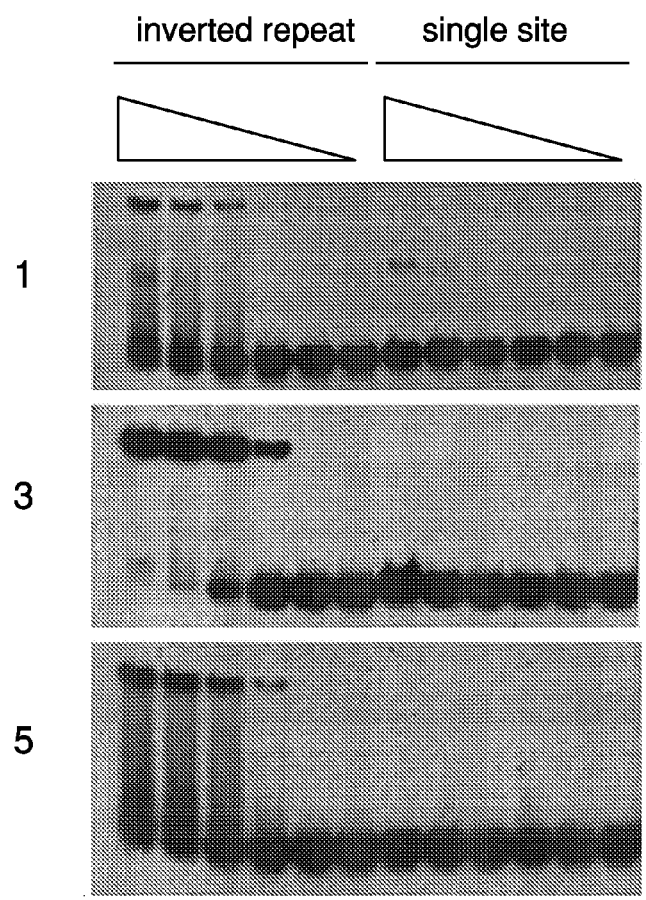
FIG. 4(A) Sequences of peptide extensions (SEQ ID NOS: 24-29) isolated from the initial selection. Numbers in parentheses give the frequency of occurrences among the 45 clones sequenced. The clones for peptide 2 included a Glu-21-to-Asp mutation in the zinc finger region that may have been partially responsible for the affinity of this peptide. (B) Gel mobility-shift assays using purified fusion peptides 1, 3, and 5. Protein (2.5 µM, 250 nM, 25 nM, 250 pM, and no protein) was incubated with DNA containing either an inverted repeat of Zif12 sites or a single Zif12 site and then electrophoresed through native polyacrylamide gels. The reduced mobility of the inverted repeat probe in the presence of protein indicates the formation of protein-DNA complexes. Similar results were obtained with fusion peptides 2 and 6. Binding of peptide 4 depend on disulfide bond formation.

To assess their DNA-binding activity, peptides obtained in these initial selections were expressed in *Escherichia coli* (as fusions with Zif12), purified, and tested in gel mobility-shift assays (FIG. 4B). These fusion peptides bound specifically to duplex DNA containing an inverted repeat of the Zif12 sites, showing little or no activity with DNA containing a single site. The complexes with the inverted-repeat site all migrated similarly in the gel, with a mobility for the complexes that was consistent with the formation of dimers. The isolated Zif12 zinc finger domains did not shift either DNA site under these conditions.

TABLE 1

Affinities for DNA duplexes containing the inverted repeat site 5'-TGGGCGCGCCCA-3' (SEQ ID NO: 20).

| Peptide | Half-maximal binding, nM | $K_d, M^2$ |
|---------|--------------------------|------------|
| Zif12   | 9,600                    | 9.2 (±3.3) × $10^{-11}$ |
| 1       | 410                      | 1.7 (±0.44) × $10^{-13}$ |
| 3       | 37                       | 1.4 (±0.04) × $10^{-15}$ |
| 5       | 440                      | 1.9 (±0.13) × $10^{-13}$ |
| 1*      | 15                       | 2.3 (±0.35) × $10^{-16}$ |
| 5*      | 12                       | 1.4 (±0.27) × $10^{-16}$ |

Half-maximal binding is given in concentration of monomer. $K_d$ represents that for binding of a dinner. Data shown are mean (±SD) for three independent experiments.

Quantitative DNA-binding assays were used to investigate further the affinity and cooperativity for binding of several of these fusion proteins (Table 1). When the DNA contained an inverted repeat of the Zif12-binding site, fusion peptides 1, 3, and 5 bound substantially tighter than did Zif12 alone. Scatchard analysis demonstrated that binding of these peptides to the inverted repeat is second order with respect to protein, as expected for a species that exists as a monomer in solution, but that binds the DNA site as a dimer. (This analysis also showed that Zif12 binds the inverted repeat with slight cooperativity, but the data for Zif12 were more consistent with a first-order than a second-order reaction.).

Figure 5:
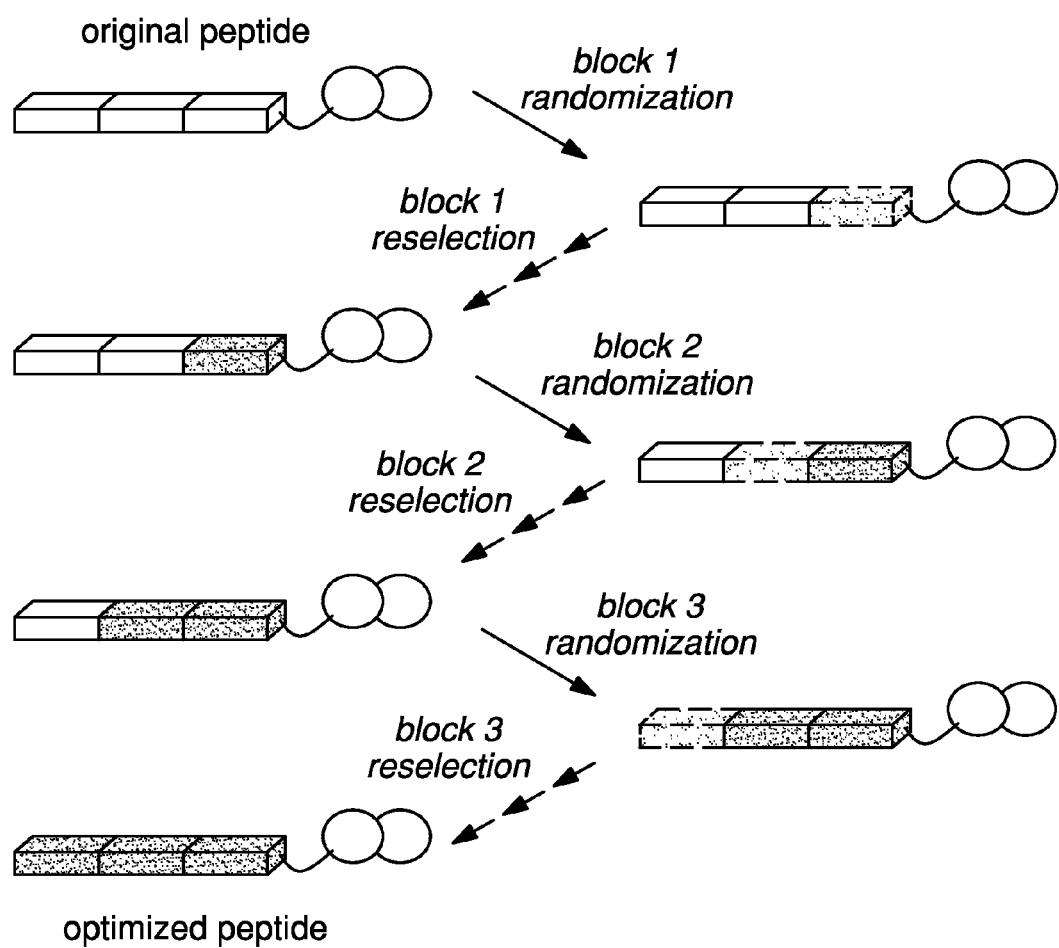
FIG. 5. Overall scheme for sequential reoptimization of peptides. A 15-residue peptide obtained from the initial selection was divided conceptually into three blocks of 5 amino acids (aa) each and reoptimized in three steps. In the first step, the five-residue block closest to the fingers was completely randomized, with the other 10 aa held constant. Phage display of the new fusion proteins, with six to nine selection and amplification cycles, was used to obtain the best sequences from this pool. In the second reoptimization step, the central five-residue block was completely randomized, with the finger-proximal region held constant as the newly optimized sequence and the finger-distal region corresponding to the initially selected sequence. The best sequences from this pool were obtained again via phage display with a series of selection and amplification cycles. In the final reoptimization step, the finger-distal five-residue block was completely randomized and then reselected in the context of the two other reoptimized blocks.

Because our initial search could test only a tiny fraction of all possible 15-mer sequences, we expected that we could use our initial peptides as a starting point for the "evolution" of even more efficient dimerization motifs. We developed a sequential reoptimization strategy (FIG. 5) to try to improve the dimerization properties of fusion peptides obtained in our initial selections. Our strategy conceptually divided each 15-mer peptide into three five-residue blocks. In the first reoptimization step, we completely randomized the block closest to the fingers (with the other residues held constant) and selected for sequences with even higher affinity for the symmetric DNA site. The second and third blocks were randomized and reselected in subsequent reoptimization steps. During this procedure, we took several measures to increase the stringency of the selection conditions. The concentration of DNA target was lowered 40-fold over the course of the reoptimization steps, and the temperature of the binding reaction was raised from 23 to 37° C. In the third reoptimization step, a mutation was introduced into one of the Zif12 sites to weaken the protein-DNA interface (and this create greater selective pressure for effective dimerization). In the later cycles of each reoptimization step, phage were present in excess of the DNA target, forcing direct competition among the remaining phage for the limited number of binding sites and, thus, favoring selection of the tightest-binding sequences from each pool.

Progress of the sequential reoptimization protocol was monitored by sequencing phage pools at a number of stages. The full reoptimization strategy was applied to fusion peptides 1 and 5 from the initial selections (FIG. 6). Peptide 3, which also was reoptimized, yielded variants that appeared to form higher-order oligomers and therefore was not studies in detail. We typically used six to nine selection-amplification cycles for the reoptimization of any particular five-residue block. One of the final sequences—resembling the consensus for the set—was then chosen for use in the next step. In some cases, choosing a consensus sequence was complicated somewhat by the presence of spurious mutations (FIG. 6) in nonrandomized portions of the peptide. Because such mutations probably conferred some other selective advantage (independent of the peptide block targeted for reoptimization), clones carrying them were not used in assigning a consensus. The final selected peptides—with all three five-residue blocks reoptimized—were designated as 1* and 5* to indicate that they had been obtained by sequentially reoptimizing peptides 1 and 5. A variant form of peptide 1* also was chosen for further analysis (FIG. 6).

The reoptimized fusion peptides were expressed and purified, and their DNA-binding properties were assessed with quantitative gel-shift assays (Table 1). For fusion peptides 1* and 5*, half-maximal DNA binding was observed with peptide concentrations in the nanomolar range, demonstrating that the reoptimization process produced peptides with significantly higher affinity. The variant form of peptide 1* also bound very tightly, but appeared to form higher-order complexes with the DNA, and this peptide was not studied further.

Sedimentation equilibrium experiments were conducted with several fusion peptides to determine their oligomeric state in solution. Peptide 1*, peptide 5, and the isolated Zif12 domain were monomeric at all concentrations tested (up to ≈100 µM). Peptide 5* was monomeric at concentrations up to 50 µM, above which the peptide appeared to form higher-order aggregates (apparently tetramers). These results confirmed that our selected peptides exist as monomers in solution at the concentrations used in the DNA-binding assays.

Discussion

Protein-protein interactions play important roles in protein-DNA recognition by facilitating cooperative binding. In this project, we sought to "evolve" stable zinc finger dimerization elements starting from libraries of random polypeptides. Broadly speaking, our goals in this study were threefold: (i) to gain some impression about the frequency of functional dimerization elements in a pool of random polypeptides; (ii) to explore the utility of a sequential block-reoptimization strategy to improve the activity of selected peptides; and (iii) to generate dimerization elements for zinc finger proteins that may be used in future efforts to create designer DNA-binding proteins for applications in gene therapy.

Given the length of the random peptides tested in this study, phage display allows one to search only a tiny fraction of the relevant sequence space. We screened about $10^8$ sequences from each library, but there are $10^{19}$ possible 15-mers and $10^{39}$ possible 30-mers. The success of the initial screen, which yielded several different peptides that mediate dirnerization, suggests that such peptides are relatively "common" in sequence space. Zhang et al. (19) have isolated dimerization elements by fusing random fragments of the yeast genome to the DNA-binding domain of lambda repressor and selecting fusion proteins that reconstitute repressor activity. This group reached similar conclusions regarding the frequency of functional dimerization domains. Our findings may help explain why dimerization elements are so common and have such diverse sequences in natural DNA-binding proteins. The peptides that we have isolated may be analogous—in an evolutionary and functional sense—to the peptide extensions that are responsible for heterodimerization of certain homeodomain proteins (20-22).

It is interesting that we obtained only 15-mer extensions in our initial selection, although the starting library consisted of equal numbers of fusion proteins with 15- and 30-residue N-terminal extensions. At this stage, the significance of this observation remains unclear. Our sample may be too small to determine the relative effectiveness of 15-mers and 30-mers as dimerization units, and it is possible that problems with processing and display on the phage surface become more severe with large random peptides. Considering the number of selection-amplification cycles used, even a modest difference in propagation efficiency between 15-mers and 30-mers could have resulted in substantial bias in the final pool.

During the natural evolution of a protein, many sequence variants are tested for improved activity. We adopted a generally similar strategy, searching sequences related to the initial peptides, but we generated variants in a distinctive way. The peptides were reoptimized in three steps, with each step involving an exhaustive search of a five-residue sequence block. Envisioning that the zinc fingers would provide a relatively rigid structural framework, we began reoptimization with the five-residue block closest to the fingers and then proceeded outward. Because we completely randomize each block when it is reoptimized, our procedure systematically searches a large number of sequence variants that can differ dramatically from the initial peptide, and the final sequence may be altered (potentially) at every position. In this respect, our strategy encompasses a broader search than more traditional mutagenesis schemes, which often involve creating variants of the initial sequence with a limited number of changes (see ref. 2 for a theoretical discussion of different mutagenesis strategies). Given the number of residues that are randomized in an reoptimization step, it is even possible that the overall fold of a reoptimized peptide will be different from the fold of the original peptide.

Our "sequential block reoptimization" strategy was applied successfully to several fusion peptides and yielded variants with high DNA-binding affinity (Table 1). Assuming that the binding of the isolated Zif12 domain reflects the binding of the Zif12 moiety in the selected fusion peptides, the binding energy contribute by each peptide extension is represented by the free energy of binding for the fusion peptide minus that for Zif12 alone. The contribution of the peptide extension includes the energy of dimerization as well as any energy derived from contacts between the peptide extension and the DNA. For peptides 1* and 5*, this value is about 7.3 kcal/mol (i.e., 20.0 kcal/mol-12.7 kcal/mol). This is more than twice that contributed by peptides 1 and 5 (≈3.5 kcal/mol), which had been obtained in the initial selections. The DNA-binding affinities of our optimized peptides (1* and 5*) are roughly comparable to those of ZFGD1, a rationally designed chimeric protein composed of Zif12 fused to a 60-residue linker and coiled-coil dimerization domain from Ga14(1). It appears that, in some situations, such small peptides may be able to functionally replace larger protein domains.

In the course of our reoptimizations, we may have approached a practical limit of our selection system. Although our selections employed a "monovalent" display format (23), we assume that most of the phage that bound in a given cycle actually were bivalent. (Presumably, monovalent phage predominate in the sample, but the fraction of retained phage was always less than 1%, and it is certainly possible that these are predominantly bivalent phage.) Phage displaying two copies of the peptide-zinc finger fusion would bind more tightly to the dimeric site than their monovalent counterparts, because the peptides attached to the same phage would be tethered at a high "effective concentration." The opportunity for bivalent binding presumably aided the initial selections but may complicate reoptimization. As higher-affinity dimers arise, peptides on bivalent phage may, aided by the high "effective concentration," form dimers even in the absence of DNA, and this would eliminate any basis for selecting tighter dimers. In addition, as dimer interfaces become more stable, and as members of the phage pool become more similar (in the reoptimizations, all sequences in a pool share at least 10 residues), there also is an increased probability of two slightly different monovalent phage binding to a single DNA target molecule. Such phage heterodimers could be reduced by lowering the concentration of phage. Finally, selection for high-affinity dimers may isolate some peptides with alternative oligomerization states. Several of our reoptimized sequences appeared to form higher-order complexes, and it is interesting in this context that design studies with self-associating amphipathic helices have shown that subtle sequence changes can dramatically alter the oligomeric state (24). Similar adventitious effects may have occurred with some of our selected peptides, or there may be binding modes that permit two bivalent phage to occupy the same DNA site.

Investigating the structural details of the complexes presented here should yield basic insights into how dimerization can be achieved with short peptides. The different peptide "classes" uncovered in this study share no obvious sequence similarity with each other or with natural dimerization elements indicating that we have isolated several distinct and novel motifs. Furthermore, secondary structure predictions (25) for our sequences indicate very different structural propensities for the different peptides. The selected peptides might fold into different structures or pack in different ways at the dimer interface.

Although we tend to envision dimerization in terms of peptide-peptide interactions, cooperative binding also would be obtained if the peptide extension from one fusion protein reached across the center of the DNA site and bound to the zinc finger domain of a symmetry-related molecule. In principle, a peptide also might induce dimer formation by promoting domain swapping (26) between substructures of two Zif12 monomers when they are bound to adjacent sites on the DNA. Finally, we note that improved DNA-binding affinity could result from additional peptide-DNA contacts (the Lys or Arg residues that are preferred at the position immediately preceding the fingers may play some such role), but these contacts would not be expected to contribute to the observed cooperativity of binding.

The selection of dimerization elements for zinc fingers demonstrates that these elements are relatively common in sequence space and reemphasizes the utility of screening random polypeptide libraries when developing proteins with desired activities. We have shown that a sequential reoptimization strategy can generate peptides with significantly higher activity, and peptide sequences such as those described here may prove useful for other zinc finger and DNA-binding protein design studies. There may be practical advantages to using these selected peptides (as opposed to known dimerization motifs such as coiled coils), because it seems less likely that these peptides will "crossreact" by heterodimerizing with natural dimerization interfaces presented by proteins in the cell. Further characterization of these novel motifs should broaden our understanding of macromolecular recognition and protein evolution by providing interesting comparisons to nature polypeptide sequences involved in dimerization and cooperative binding.

Reference Cited in Example 1
1. Pomerantz, J. L., Wolfe, S. A. & Pabo, C. O., (1998) *Biochemistry* 37, 965-970.
2. Smith, P. & Petrenko, V. A. (1997) *Chem.Rev.* 97, 391-410.
3. Lowman, H. B. (1997) *Annu. Rev Biophys. Biomol Struct.* 26, 401-424.
4. Cunningham, B. C. & Wells, J. A. (1997) *Curr. Opin. Struct. Biol.* 7, 457-462.
5. Wrighton, N. C., Farrell, F. X., Chang, R., Kashyap, A. K., Barone, F. P., Mulcahy, L. S., Johnson, D. L., Barrett, R. W., Jolliffe, L. K. & Dower, W. J. (1996) *Science* 273, 458-463.
6. Livnah, O., Stura, E. A., Johnson, D. L., Middleton, S. A., Mulcahy, L. S., Wrighton, N. C., Dower, W. J., Jolliffe, L. K. & Wilson, I. A. (1996) *Science* 273, 464-471.
7. Rebar, E. J., Greisman, H. A. & Pabo, C. O. (1996) *Methods Enzymol.* 276, 129-149.
8. Pavletich, N. P. & Pabo, C. O. (1991) *Science* 252, 809-817.
9. Rebar, E. J. & Pabo, C. O. (1994) *Science* 263, 671-673.
10. Carey, J. (1991) *Methods Enzymol.* 208,103-117.
11. Brenowitz, M., Senear, D. F., Shea, M. A. & Ackers, G. K. (1986) *Methods Enzymol.* 130, 132-181.
12. Klemm, J. D. & Pabo, C. O. (1996) *Genes Dev.* 10,27-36.
13. Laue, T. M., Shah, B. D., Ridgeway, T. M. & Pelletier, S. L. (1992) in *Analytical Ultracentrifugation in Biochemistry and Polymer Science*, eds. Harding. S. E., Rowe, A. J. & Horton, J. C. (*R. Soc. Chem. Cambridge, UK.*), pp. 90-125.
14. McRorie, D. K. & Voekler, P. J. (1993) *Self-Associating Systems in the Analytical Ultracentrifuge* (Beckman Instruments, Fullerton, Calif.).
15. Laue, T. M. (1995) *Methods Enzymol.* 259,427-452.
16. Johnson, M. L., Correia, J. J., Yphantis, D. A. & Halvorson, H. R. (1981) *Biophys. J.* 36,575-588.
17. Christy, B. A., Lau, L. F. & Nathans, D. (1998) *Proc. Natl. Acad. Sci. USA* 85,7857-7861.
18. Altschul, S. F., Gish, W., Miller, W., Myers, E. W. & Lipman, D. J. (1990) *J. Mol. Biol.* 215, 403-410.
19. Zhang, Z., Murphy, A., Hu, J. & Kodadek, T. (1999) *Curr. Biol.* 9,417-420.
20. Li, T., Stark, M. R., Johnson, A. D. & Wolberger, C. (1995) *Science,* 270, 262-269.
21. Tan, S.& Richmond, T. J. (1998) *Nature (London)* 391-660-666.
22. Passner, J. M., Ryoo, H. D., Shen, L., Mann, R. S. & Aggarwal, A. K. (1999) *Nature (London)* 397,714-719.
23. Bass, S., Greene, R. & Wells, J. A. (1990) *Proteins Struct. Funct. Genet.* 8, 309-314.
24. Harbury, P. B., Zhang, T., Kim P. S. & Alber, T., (1993) *Science* 262, 1401-1407.
25. Rost, B. & Sander, C. (1993) *J. Mol. Biol.* 232, 584-599.
26. Bennett, M. J., Schlunegger, M. P. & Eisenberg. D. (1995) *Protein Sci.* 4,2455-2468.

Example 2

Structural Analysis of a Zinc Finger Protein Dimer

Protein-protein interactions are crucial for the assembly and function of many protein-DNA complexes. To explore the structural possibilities for such interactions, we previously selected short peptide extensions that facilitate cooperative binding of zinc finger domains, and we have now determined the crystal structure of one such complex. We find that this peptide extension mediates dimerization by reaching across the twofold axis and contacting the exposed surface of the finger that is bound to the neighboring site. The overall features of this complex are remarkably similar to those seen with some homeodomain heterodimers. Addition of such contacts may provide a readily accessible route (both in vivo and in vitro) for enhancing affinity and specificity of recognition.

Protein-protein interactions can play critical roles in the formation of higher-order protein-DNA complexes in the combinatorial control of gene expression (for example, see, Ptashne, A Genetic Switch: Phage Lambda and Higher Organisms (Cell Press, Cambridge, Mass., ed. 2, 1992; Wolberger Ann. Rev. Biophys. Biomol. Struct. 28, 29 (1999)). Such cooperative interactions can increase the affinity and/or specificity of protein-DNA recognition, change the concentration dependence of binding, or recruit other regulatory proteins to the DNA site. One interesting example of this kind of contact involves cooperative binding of homeodomain heterodimers. Crystallographic studies of the yeast MATα1/α2 complex revealed that a carboxy-terminal peptide tail from contacts (peptide-peptide, peptide-protein, or peptide-DNA) that might mediate this binding. To determine what interactions were made by the peptide, we crystallized and solved the structure of this complex. We obtained excellent crystals of the homodimer bound to a symmetric DNA site, prepared heavy atom derivatives by synthesizing iodine-substituted DNA oligos, and then solved the structure and refined it to 2.35 Å resolution (Table 2).

TABLE 2

| Data Collection and MIR Phasing | | | | |
|---|---|---|---|---|
|  | Native-1 | IdU-2 | IdC-8 | Native-2 |
| Resolution, Å | 20-2.7 | 20-3.0 | 20-2.7 | 20-2.35 |
| Measured reflections | 85,644 | 87,027 | 97,771 | 191,628 |
| Unique reflections | 30,331 | 22,186 | 29,250 | 45,805 |
| Completeness, % | 100 (99.9) | 99.9 (99.5) | 99.9 (100) | 99.9 (99.8) |
| $R_{sym}$, % | 7.0 (38.4) | 14.0 (56.0) | 13.2 (74.7) | 8.1 (34.5) |
| reflections with I/σ (I) > 2, % | 77.9 (40.8) | 82.2 (46.9) | 64.4 (30.3) | 89.1 (65.4) |
| Twin fraction | 0.05 | 0.2 | 0.08 | 0.26 |
| $R_{iso}$, % |  | 17.0 | 25.9 |  |
| Phasing power |  | 1.02 | 0.83 |  |
| Figure of merit, MIR | 0.33 |  |  |  |

Values in parentheses for highest resolution shell.

| Refinement | | | |
|---|---|---|---|
| Resolution range, Å | 20-2.35 |  |  |
| Reflections, F > 2σ (F) | 38,060 | average B-value (Å$^2$) | 41.4 |
| # of Non-H atoms | 5329 | rmsd ΔB-values, bonded atoms (Å$^2$) | 4.1 |
| $R_{work}$, % | 21.0 | rmsd from ideal, bond lengths, Å | 0.007 |
| $R_{free}$, % | 25.6 | rmsd from ideal, bond angles, ° | 1.1 |

MATα2 binds to an exposed hydrophobic path on MATα1, thereby enhancing the affinity and specificity of recognition (Li et al. Science 270, 262 (1995)). Structural studies have also shown that the *Drosophila* Ultrabiothroax and human HoxB1 homeodomain proteins contact their partners (Extradenticle and Pbx1, respectively) through a conserved hexapeptide that packs against a hydrophobic path on the neighboring homeodomain (Passner et al. Nature 397, 714 (1999); Piper et al. Cell 96, 587 (1999)).

Figures 8A, 8B:
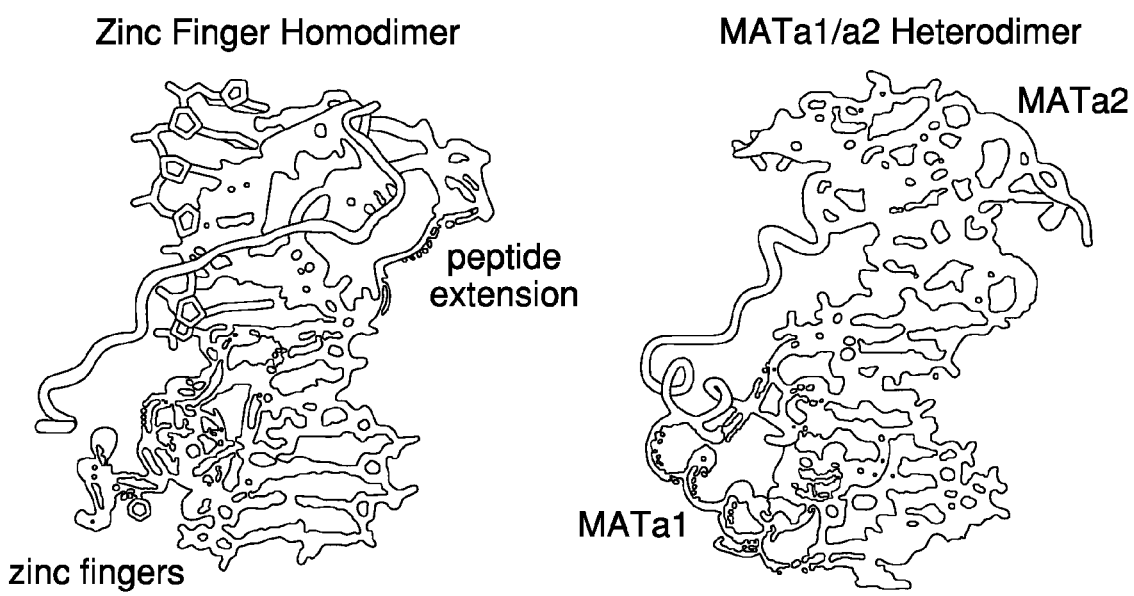
FIG. 8. Crystal structure of our zinc finger homodimer and comparisons with the MATa1/α2 homeodomain heterodimer. (A) Overview of our homodimer complex. The protein monomers bind in a head-to-head orientation on the DNA; the peptide extension and zinc fingers for the monomers are labeled. The complex is approximately symmetric with a twofold axis that goes through the center of the DNA and is perpendicular to the plane of the page. There are two zinc fingers in each monomer, and these bind essentially as observed in the wild-type Zif268 complex (finger 2 for each monomer is hard to see in this figure since it is almost directly behind finger 1 in this view of the complex). (B) Crystal structure of the MATa1/α2 heterodimer-DNA complex as determined by Wolberger and colleagues, *Ann Rev Biophys. Biomol. Struct.* 28, 29 (1999); Li et al., Science 270, 262 (1995). A peptide extension from the MATα2 homeodomain contacts an exposed hydrophobic surface on the MATa1 homeodomain to facilitate cooperative binding.

It is not yet known how common such peptide-protein contacts are in higher order protein-DNA complexes. However, we have found very similar interactions in the crystal structure of a peptide-zinc finger fusion—previously obtained by in vitro evolution—that binds cooperatively to DNA (FIG. 8). This fusion protein had been selected and optimized in several different stages (Wang and Pabo, Proc. Nat. Acad. Sci. USA 96,9568 (1999)). We had begun these experiments by adding random 15-residue peptide extensions to the N-terminus of fingers one and two of Zif268 (Pavletich and Pabo Science 252, 809 (1991)) and had used phage display to select fusion proteins that formed stable homodimers on a palindromic DNA site. Using these selected peptides as a starting point, we then proceeded with several rounds of randomization and reselection (under more stringent conditions) to obtain peptides that further stabilized homodimer formation. The reoptimized fusion protein that was chosen for further structural study designated 1* in our previous paper (Wang and Pabo, Proc. Nat. Acad. Sci. USA 96,9568 (1999) is monomeric in solution and yet binds DNA primarily as a dimer. Half-maximal DNA binding occurs at 15 nM protien, while the corresponding Zif1-Zif2 construct (without peptide extension) binds at 10 μM.

The peptide extension obtained in this experiment had been selected to facilitate cooperative binding of the zinc finger domains, but there was no further constraint on the type of Table 2: Crystallographic Analysis. The zinc finger fusion peptide (containing an NH3-Met-Glu-Pro leader peptide, the 15 residues of the selected peptide extension (Wang et al. Proc. Natl. Acad. Sci. USA 90, 9568 (1999)), and residues 4 to 60 of Zif268 (Pavletich, supra) and was overexpressed, purified and prepared for crystallization essentially as described previously for Zif268 variant peptides in Elrod-Erickson et al. Structure 6, 451 (1998)) and was cocrystallized with a 14-base pair DNA duplex (the self-complementary oligonucleotide 5'-ATGGGCGCGCCCAT-3' (SEQ ID NO:21) was purified as described previously in Klemm et al., Cell 77,21 (1994) and annealed at a high concentration (3 mM in duplex) to favor formation of intermolecular duplexes over intramolecular hairpins. Derivative olioigs contained either 5-iodouracil at position 1 or 5-iodocytosine at position 8) using PEG 4000 as the precipitant. Equal volumes of protein (1.1 mM in dimer) and duplex DNA (1.5 mM) were mixed, and complexes were solubilized with the addition of NaCl to 0.4 M. Crystals were grown in an anaerobic chamber using hanging drop vapor diffusion from drops containing the complex and an equal volume of the well solution (13-20% PEG-4,000/50-150 mM NaCl/10 mM MgCl$_2$/50 mM MES, pH 6.2). The crystals were soaked for approximately 5 minutes in a solution containing equal volumes of well solution and cryoprotectant solution 38% glycerol/20% PEG-4,000/100 mM NaCl/50 mM MES, pH 6.2) and flash-cooled in a stream of cold nitrogen (126 K). The crystals form in spacegroup P3$_1$ with cell dimensions a=b=86.2 Å, c=133.0 Å. Diffraction data (for Native-1 and the derivatives) were first collected on cryocooled crystals using a rotating anode X-ray generator and an R-Ax 8 IV image plate system. Data were processed with the HKL suite (Z. Otwinowski, W. Minor, *Methods Enzym.* 276, 307 (1997)). The crystals exhibited partial merohedral twinning, and the twin fraction in each crystal (as listed in the Table) was estimated according to the procedure of Yeates (T. O. Yeates, *Methods Enzym.* 276, 344 (1997)). Data was detwinned using the DETWIN program in the CCP4 suite (Collaborative Computational Project Number 4, *Acta Crystallogr.* D50, 760 (1994)). There are three dimer-DNA complexes per asymmetric unit (In the crystal, DNA duplexes stack end-to-end, although the basepairs at the junctions are rotationally offset so that pseudocontinuous helices are not formed. DNA stacks run along each crystallographic $3_1$ screw axis. Thus, there are three stacks of three complexes in each unit cell, and complexes within each stack are crystallographically related. The three crystallographically independent complexes (and the two crystallographically independent halves of each complex) are very similar to one another. However, one of the protein monomers shows poor density for several residues at the N-terminus (Asn 93 to Val 98) and for finger 2, especially in the beta hairpin region. (There are few crystal contacts in these regions, and they therefore may be more mobile.) With these exceptions, residues Asn 93 to Thr 158 of each protein monomer and the entire DNA duplex for each complex are visible in our structure.) Iodine sites in the derivatives were located with SOLVE (T. Terwilliger, J. Berendzen, *Acta Crystallogr.* D55, 849 (1999)), and MIR phases (SOLVE located 6 of 6 sites in derivative IdU-2 and 5 of 6 sites in derivative IdC-8. Since there were three copies of each duplex in the asymmetric unit, and because each duplex was expected to have the same distribution of iodine sites, superimposing corresponding sets of heavy atom positions allowed us to predict the remaining heavy atom site and to determine approximate noncrystallographic symmetry (NCS) operators) were improved by solvent flattening and noncrystallographic symmetry (NCS) averaging using DM (Collaborative Computational Project Number 4, *Acta Crystallogr.* D50, 760 (1994)). The resulting experimental electron density map was readily interpretable, and a model was built with O (T. A. Jones, J.-Y. Zou, S. W. Cowan, M. Kjeldgaard, *Acta Crystallogr.* A47, 110 (1991)). We refined the model to 2.7 Å with X-PLOR (A. T. Brunger, *X-PLOR Version 3.1: A System for X-ray Crystallography and NMR* (Yale University Press, New Haven, Conn., 1992)) using the Native-1 data set. As refinement progressed, we relaxed NCS constraints to restraints and then eliminated NCS restraints altogether, refined grouped B-factors, and applied a bulk solvent correction. We then collected an additional data set (Native-2) at the National Synchrotron Light Source on Beamline X4A ($\lambda$=1.0093 Å), and this data was detwinned and merged with the detwinned Native-1 data. Using this higher-resolution data set, we proceeded with further positional refinement and individual, restrained B-factor refinement and also added 319 water molecules to the model. In the final model, 90.9% of the residues lie in the core regions of the Ramachandran plot and the remaining residues occupy additional allowed regions.

As expected, our complex has two protein monomers arranged symmetrically on the palindromic DNA site that had been used in the selections. The overall structures and docking arrangements of the two zinc fingers on each half site are similar to those observed in the Zif268-DNA complex (Pavletich et al. Science 252, 809 (1991); Elrod-Erickson et al., Structure 4, 1171 (1996)). Phosphate contacts made by two residues (Lys 101 and Arg 103) from each peptide extension augment the zinc finger-DNA interactions. Interactions between Arg 103 and phosphate 5 appear especially strong, as we see clear density for this side chain. In the wild-type Zif268 structure, an arginine at the corresponding position (residue 3 in the crystal structure of Pavletich, supra) makes analogous contacts. We also observe a contact between Lys 101 and phosphate 6, although this side chain is less well-ordered.

Figure 9:
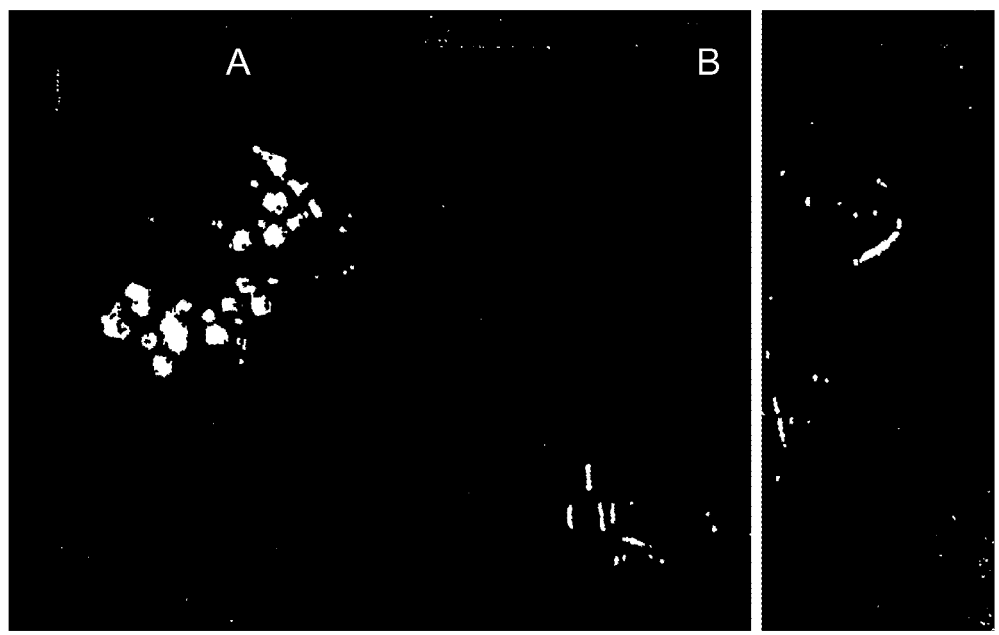
FIG. 9. Peptide-protein contacts at the dimer interface of our zinc finger complex. For simplicity, only the contacts in one half of the symmetric dimer are shown; an equivalent set of contacts is seen in the other half of the dimer. (A) View of the dimer interface showing the peptide extension fitting against the zinc finger (surface representation). (B) Diagram highlighting key residues of the peptide extension and zinc finger 1 at the dimer interface.

However, the rest of the peptide extension stretches away from the attached zinc finger domains, reaching past the center of the binding site and making extensive interactions with zinc finger 1 from the symmetry-related molecule. The zinc finger surface contacted by the peptide involves a region where the $\alpha$ helix packs against the first strand of the $\beta$ sheet, and this exposed surface lies just above the secondary strand of the DNA (FIG. 9A). This overall arrangement shows a striking similarity to the interactions found in the homeodomain heterodimers that have been studied crystallographically (FIG. 8).

As observed with the homeodomain heterodimers, hydrophobic interactions dominate the peptide-protein interface in our complex (FIG. 9B). In describing these interactions, we use a numbering scheme that follows the convention used in the wild-type Zif268 structure (residue numbers 104 to 160 in the crystal structure correspond to residues 4 to 60 in the zinc finger sequence, Pavletich and Pabo, Science 252, 809 (1991)), and thus our 15-residue peptide extension is numbered as H89-PMNNLLNYVVPKM-R103 (SEQ ID NO:22) (to indicate that this is the preceding region of the polypeptide chain in our new protein). Near the twofold axis at the center of the site, the side chain of Pro 104 packs against Pro 104' and Tyr 105' (from the other subunit), while Met 102 interacts with Pro 104, Pro 104', and Tyr 105'. In this region, there is also a hydrogen bond between the carbonyl oxygen of Ser 117 and the hydroxyl group of Tyr 105'. Further outward along the peptide, the side chains of Val 99 and Pro 100 form a nonpolar surface that supports the side chain of Tyr 97 (which also interacts with Leu 94). Leu 94, Leu 95, Tyr 97, and Val 99 of the peptide extension contact a number of residues in zinc finger 1 of the other monomer and thus form a key part of the dimer interface. Leu 94 fits into a hydrophobic pocket formed by zinc finger residues Pro 108', Val 109', Ile 126', His 129', and Thr 130. Leu 95 contacts nonpolar groups on the side chains of Thr 130' and Gln 132'; Tyr 97 touches Pro 108' and Ile 126', and Val 99 interacts with Try 105', Ser 199', Leu 122', Thr 123', and Ile 126'. Along the edges of this extensive, hydrophobic interface, there are several bridging water molecules, but the water-mediated interactions that we observe are not conserved among the crystallographically independent copies of the dimer interface.

Our structure has a number of interesting implications for understanding zinc-finger DNA interactions and for understanding the origin of cooperativity among DNA-binding proteins. One of the most important observations is that relatively weak interactions between a peptide extension and the surface of a neighboring protein—contacts which are not sufficient to give stable dimers in solution—can still dramatically stabilize the corresponding protein-DNA complexes. Both the peptide and the surface it recognizes are present at high "local concentrations" when these proteins bind to adjacent sites on the DNA. Because these peptide extensions bind in the context of existing protein-DNA complexes, they do not need to have prefolded structures with a precise fit or to provide much energy. (The binding energy of the protein-DNA interaction can help overcome the entropy losses that otherwise would be involved with dimer formation.) We imagine that such structures represent a readily accessible "evolutionary path" for generating cooperativity in the formation of higher-order protein-DNA complexes, and our selection studies have shown that such peptides are rather common in pools of random peptide sequences (Wang and Pabo, supra). It appears that a variety of such peptide-protein contacts use similar structural principles. For example, there are substantial differences between the MATα1/α2 (Li et al., supra) and the Ultrabithorax/Extradenticle (Passner et al., supra) complexes (with respect to the structure of the extension and the arrangement of the homeodomains on the DNA), but the underlying principles in both cases seem quite similar (At this stage, we do not know whether the peptide-protein contacts in different homeodomain heterodimers arose by convergent or divergent evolution).

Figures 7A, 7B:
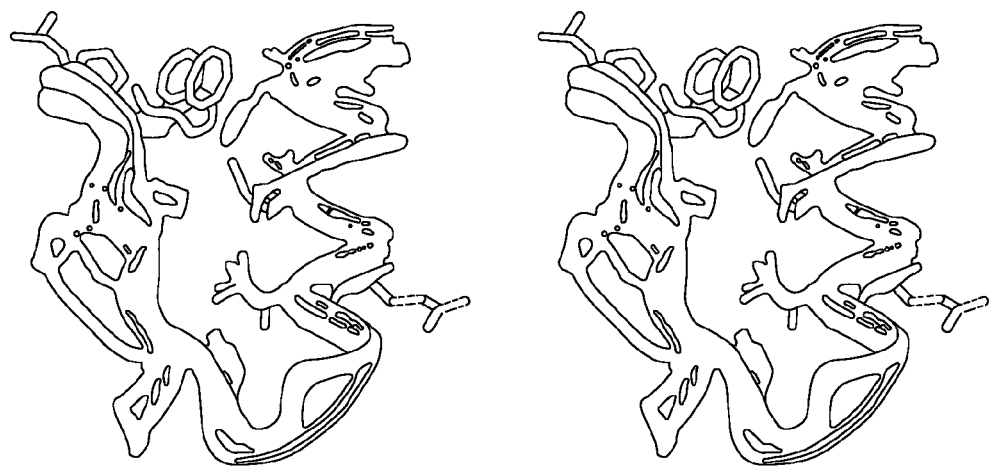
FIG. 7: Comparison of the contact surfaces of various zinc fingers. Zif268 finger 1 (SEQ ID NO:80), GLI finger 1 (SEQ ID NO:81), GLI finger 2 (SEQ ID NO:82), and SW15 finger 1 (SEQ ID NO:83) are shown. (A) Stereoview of a superposition of the four fingers. Because of the different lengths of the fingers, the superposition aligned C atoms of residues 104-114 and 116-127 of Zif finger 1 with those of residues 3-13 and 15-26 of GLI finger 1; residues 105-114 and 116-130 of Zif finger 1 with 37-46 and 51-65 of GLI finger 2; and residues 104-130 of Zif finger 1 with 31-57 of SWI5 finger 1. Side chains on each finger that are involved in hydrophobic contacts at the corresponding protein-protein interface have been rendered in stick representation. (Coordinates for GLI and SW15 are from Pavletich *Science* 261, 1701 (1993); Dutnall, *Structure* 4, 599 (1996).) (B) Alignment of the sequences of the fingers, with interacting residues boxed. The portion of Zif268 shown here corresponds to residues 104 to 130 in the crystal structure.

A number of reports have described biochemical experiments indicating protein-protein interactions mediated via Cys2-His2 zinc finger domains (MacKay, Trends Biochem. Sci. 23, 1 (1998)), and it seems quite plausible that the hydrophobic surface used in or complex may be involved in some of these other interactions. In this regard, there are interesting parallels between the contact surface exploited by our selected peptide and protein-protein interaction surfaces observed with the GLI and SWI5 zinc finger proteins. The structure of the previously reported GLI zinc finger-DNA complex (Pavletich et al., Science 261, 1701 (1993) showed that GLI finger 1 makes no protein-DNA contacts, but instead interacts extensively with GLI finger 2. Protein-protein contacts involving zinc fingers were also observed for the SWI5 DNA-binding domain, which includes an N-terminal extension that folds into an additional strand and an α helix that packs against SWI5 finger 1 (Dutnall et al., Structure 4, 599 (1996)). Strikingly, the interactions in each case (the surfaces used by GLI finger 1, by GLI finger 2, and by SWI5 finger 1) all involve hydrophobic contacts to sites that are nearly identical to the region of Zif268 finger 1 contacted in our current structure (FIG. 7). It thus appears that this surface of the zinc finger is particularly well suited for associating with other protein structures, and likely plays a similar role in many other complexes. The correspondence of these structures is interesting since—in other cases—it has been shown that peptides selected by phage display targeted natural protein-protein interaction surfaces (Livnah, et al., Science 273, 464 (1996); DeLano et al., Science 287, 1279 (2000)).

Dimerization modules of the type reported here may be useful when designing new zinc finger proteins that recognize extended binding sites, and such modules provide effective alternatives to covalent linkage (Liu et al. Proc. Natl. Acad. Sci. USA 94, 5525 (1997); Kim et al., Proc. Natl. Acad. Sci. USA 95, 2812 (1998)) or to the use of coiled-coil dimerization domains (Pomerantz et al., Biochemistry 37, 965 (1998)). Our results indicate that this peptide extension can be used with Zif variants that recognize alternative sites (i.e., the structure suggests that the peptide-protein contacts responsible for cooperative binding should function relatively independently of the zinc finger-DNA contacts responsible for site-specific recognition). Many further improvements through design and/or selection also are feasible. It should be possible to (1) further optimize these peptide-protein interactions, to (2) obtain variants that stabilize head-to-tail binding of zinc finger proteins, and to (3) isolate peptides that specifically contact other proteins bound at neighboring sites. Pre-association of protein domains to adjacent regions on DNA can provide a starting point for subsequent selection or evolution of modules that allow cooperative binding or enhanced specificity. The similarity between our selected zinc finger homodimer and the homeodomain homodimers highlights the important role that peptide extensions can play in the formation of these complexes and illustrates how design, selection, and evolution can exploit common underlying physical principles. Coordinates for the crystal structure have been deposited in the Protein Data Bank (accession code 1F2I).

What is claimed is:

1. A zinc finger complex, comprising two or more fusion proteins, each fusion protein comprising a zinc finger protein that binds to DNA in a sequence-specific manner and a peptide linker, wherein the zinc finger proteins of the fusion proteins are joined to each other by specific binding of the peptide linkers, and wherein the peptide linkers are non-naturally occurring peptide linkers of 30 amino acids or less in length.

2. The zinc finger complex of claim 1, wherein the peptide linker of each fusion protein is the same.

3. The zinc finger complex of claim 1, wherein the zinc finger protein of each fusion protein has the same sequence.

4. The zinc finger complex of claim 1, wherein the peptide linker is between 8 and 25 amino acids in length.

* * * * *

```
SEQUENCE LISTING

<160> NUMBER OF SEQ ID NOS: 83

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence:  exemplary
      motif characterizing C2H2 class proteins
<220> FEATURE:
<221> NAME/KEY: SITE
<222> LOCATION: (2)..(5)
<223> OTHER INFORMATION: where Xaa is any amino acid
<220> FEATURE:
<221> NAME/KEY: SITE
<222> LOCATION: (4)..(5)
<223> OTHER INFORMATION: where Xaa may be present or absent
<220> FEATURE:
<221> NAME/KEY: SITE
<222> LOCATION: (7)..(18)
<223> OTHER INFORMATION: where Xaa is any amino acid
<220> FEATURE:
<221> NAME/KEY: SITE
<222> LOCATION: (20)..(24)
<223> OTHER INFORMATION: where Xaa is any amino acid
<220> FEATURE:
<221> NAME/KEY: SITE
<222> LOCATION: (23)..(24)
<223> OTHER INFORMATION: where Xaa may be present or absent

<400> SEQUENCE: 1

Cys Xaa Xaa Xaa Xaa Cys Xaa Xaa Xaa Xaa Xaa Xaa Xaa Xaa Xaa Xaa
1               5                   10                  15
```

```
Xaa Xaa His Xaa Xaa Xaa Xaa Xaa His
        20                  25

<210> SEQ ID NO 2
<211> LENGTH: 4
<212> TYPE: DNA
<213> ORGANISM: Artificial Sequence
<220> FEATURE:
<223> OTHER INFORMATION: Description of Artificial Sequence: D-able
      subsite
<220> FEATURE:
<221> NAME/KEY: misc_feature
<222> LOCATION: (1)..(2)
<223> OTHER INFORMATION: n = a, t, g or c
<220> FEATURE:
<221> NAME/KEY: misc_feature
<222> LOCATION: (4)
<223> OTHER INFORMATION: k = g or t

<400> SEQUENCE: 2 nngk                                                                     4

<210> SEQ ID NO 3
<211> LENGTH: 9
<212> TYPE: DNA
<213> ORGANISM: Artificial Sequence
<220> FEATURE:
<223> OTHER INFORMATION: Description of Artificial Sequence:  zinc
      finger protein bind sequence

<400> SEQUENCE: 3 ggcgtagac                                                                9

<210> SEQ ID NO 4
<211> LENGTH: 9
<212> TYPE: DNA
<213> ORGANISM: Artificial Sequence
<220> FEATURE:
<223> OTHER INFORMATION: Description of Artificial Sequence:  zinc
      finger protein bind sequence

<400> SEQUENCE: 4 ggcgacgta                                                                9

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence:  peptide
      linker

<400> SEQUENCE: 5

Thr Gly Glu Lys Pro
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:  linker

<400> SEQUENCE: 6

Gly Gly Gly Gly Ser
 1               5

<210> SEQ ID NO 7
```

```
<211> LENGTH: 8
<212> TYPE: PRT
<213> ORGANISM: Artificial Sequence
<220> FEATURE:
<223> OTHER INFORMATION: Description of Artificial Sequence: linker

<400> SEQUENCE: 7

Gly Gly Arg Arg Gly Gly Gly Ser
 1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: linker

<400> SEQUENCE: 8

Leu Arg Gln Arg Asp Gly Glu Arg Pro
 1               5

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: linker

<400> SEQUENCE: 9

Leu Arg Gln Lys Asp Gly Gly Gly Ser Glu Arg Pro
 1               5                  10

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: linker

<400> SEQUENCE: 10

Leu Arg Gln Lys Asp Gly Gly Gly Ser Gly Gly Gly Ser Glu Arg Pro
 1               5                  10                  15

<210> SEQ ID NO 11
<211> LENGTH: 25
<212> TYPE: PRT
<213> ORGANISM: Artificial Sequence
<220> FEATURE:
<223> OTHER INFORMATION: Description of Artificial Sequence: component
      finger of zinc finger protein
<220> FEATURE:
<221> NAME/KEY: SITE
<222> LOCATION: (2)..(5)
<223> OTHER INFORMATION: where Xaa is any amino acid
<220> FEATURE:
<221> NAME/KEY: SITE
<222> LOCATION: (4)..(5)
<223> OTHER INFORMATION: where Xaa may be present or absent
<220> FEATURE:
<221> NAME/KEY: SITE
<222> LOCATION: (7)..(18)
<223> OTHER INFORMATION: where Xaa is any amino acid
<220> FEATURE:
<221> NAME/KEY: SITE
<222> LOCATION: (20)..(24)
<223> OTHER INFORMATION: where Xaa is any amino acid
<220> FEATURE:
<221> NAME/KEY: SITE
<222> LOCATION: (23)..(24)
<223> OTHER INFORMATION: where Xaa may be present or absent

<400> SEQUENCE: 11
```

```
Cys Xaa Xaa Xaa Xaa Cys Xaa Xaa Xaa Xaa Xaa Xaa Xaa Xaa Xaa
 1               5                  10                  15

Xaa Xaa His Xaa Xaa Xaa Xaa Xaa His
             20                  25
```

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence: DNA
      binding domain F1

<400> SEQUENCE: 12

```
Tyr Ala Cys Pro Val Glu Ser Cys Asp Arg Arg Phe Ser Arg Ser Asp
 1               5                  10                  15

Glu Leu Thr Arg His Ile Arg Ile His Thr Gly Gln Lys Pro
             20                  25                  30
```

<210> SEQ ID NO 13
<211> LENGTH: 28
<212> TYPE: PRT
<213> ORGANISM: Artificial Sequence
<220> FEATURE:
<223> OTHER INFORMATION: Description of Artificial Sequence: DNA
      binding domain F2

<400> SEQUENCE: 13

```
Phe Gln Cys Arg Ile Cys Met Arg Asn Phe Ser Arg Ser Asp His Leu
 1               5                  10                  15

Thr Thr His Ile Arg Thr His Thr Gly Glu Lys Pro
             20                  25
```

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: DNA
      binding site

<400> SEQUENCE: 14
ggttgcagtg ggcgcgccca cagtacttga acgtaacg                      38

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: DNA
      binding site

<400> SEQUENCE: 15
cgttacgttc aagtactgtg ggcgcgccca ctgc                          34

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence: DNA
      binding site

<400> SEQUENCE: 16
tgggcgtatg ct                                                  12

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: DNA
      binding site

<400> SEQUENCE: 17
agcatacgcc ca                                                      12

<210> SEQ ID NO 18
<211> LENGTH: 57
<212> TYPE: DNA
<213> ORGANISM: Artificial Sequence
<220> FEATURE:
<223> OTHER INFORMATION: Description of Artificial Sequence: DNA
      binding site

<400> SEQUENCE: 18
ggaattcctg atcaagatct ggtcacgtcc ataggctagg catgtcaagg ctgtatg     57

<210> SEQ ID NO 19
<211> LENGTH: 57
<212> TYPE: DNA
<213> ORGANISM: Artificial Sequence
<220> FEATURE:
<223> OTHER INFORMATION: Description of Artificial Sequence: DNA
      binding site

<400> SEQUENCE: 19
gggatccact cgcgaacgcg tccttgtagt gggcgcgccc acatacagcc ttgacat     57

<210> SEQ ID NO 20
<211> LENGTH: 12
<212> TYPE: DNA
<213> ORGANISM: Artificial Sequence
<220> FEATURE:
<223> OTHER INFORMATION: Description of Artificial Sequence: inverted
      repeat site

<400> SEQUENCE: 20
tgggcgcgcc ca                                                      12

<210> SEQ ID NO 21
<211> LENGTH: 14
<212> TYPE: DNA
<213> ORGANISM: Artificial Sequence
<220> FEATURE:
<223> OTHER INFORMATION: Description of Artificial Sequence:
      self-complementary oligonucleotide

<400> SEQUENCE: 21
atgggcgcgc ccat                                                    14

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: peptide
      extension
<220> FEATURE:
<221> NAME/KEY: SITE
<222> LOCATION: (1)
<223> OTHER INFORMATION: "His" is numbered 89
<220> FEATURE:
<221> NAME/KEY: SITE
<222> LOCATION: (15)

-continued

<223> OTHER INFORMATION: "Arg" is numbered 103

<400> SEQUENCE: 22

His Pro Met Asn Asn Leu Leu Asn Tyr Val Val Pro Lys Met Arg
 1               5                  10                  15

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: DNA site
      used for affinity selection

<400> SEQUENCE: 23
gcagtgggcg cgcccacagt acttgaacgt aacg                              34

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: peptide
      1

<400> SEQUENCE: 24

Gly Gly Gly Gln Trp Leu Gly Thr Trp Glu Trp Tyr Gly Pro Lys
 1               5                  10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence:
      peptide 2

<400> SEQUENCE: 25

Tyr Glu Lys Ile Ser Val Glu Gly Ile Lys Asp Val Arg Val Arg
 1               5                  10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence:
      peptide 3

<400> SEQUENCE: 26

Asn Val Ser Ile Glu Gly Val Leu Lys Tyr Tyr Arg Gly Leu Arg
 1               5                  10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence:
      peptide 4

<400> SEQUENCE: 27

Arg Ser Cys Gly Leu Asp Tyr Glu Gly Tyr Trp Leu Lys Leu Lys
 1               5                  10                  15

<210> SEQ ID NO 28
<211> LENGTH: 15
<212> TYPE: PRT

```
<213> ORGANISM: Artificial Sequence
<220> FEATURE:
<223> OTHER INFORMATION: Description of Artificial Sequence:
      peptide 5

<400> SEQUENCE: 28

Ser Arg Trp Leu Glu Glu Glu Val Ser Arg Leu Leu Leu Leu Arg
 1               5                  10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence:
      peptide 6

<400> SEQUENCE: 29

Gly Glu Ala Leu Asp Arg Phe Glu Arg Glu Met Lys Leu Met Arg
 1               5                  10                  15

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 30

Gly Gly Gly Gln Trp
 1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 31

His Pro Met Asn Asn
 1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 32

Pro Pro Ser Thr Glu
 1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 33

Gln Lys Tyr Gly Asp
 1               5
```

-continued

```
<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 34

Glu Asn Tyr Glu Lys
 1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 35

Leu Gly Thr Trp Glu
 1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 36

Leu Leu Asn Tyr Lys
 1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 37

Leu Leu Asn Tyr Val
 1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 38

Leu Leu Asp Tyr Ile
 1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 39
```

Leu Leu Asn Tyr Ile
 1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 40

Leu Leu Gln Tyr Val
 1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 41

Leu Leu Glu Tyr Lys
 1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 42

Leu Leu Asp Tyr Val
 1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 43

Leu Leu Asn Tyr Val
 1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 44

Trp Tyr Gly Pro Lys
 1               5

<210> SEQ ID NO 45
<211> LENGTH: 5
<212> TYPE: PRT
<213> ORGANISM: Artificial Sequence
<220> FEATURE:

```
<223> OTHER INFORMATION: Description of Artificial Sequence:
      sequential block reoptimization sequence

<400> SEQUENCE: 45

His Pro Lys Met Lys
 1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 46

Pro Ala Lys Ile Arg
 1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 47

Val Pro Lys Ser Arg
 1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 48

Val Pro Arg Leu Lys
 1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 49

Ala Pro Lys Leu Arg
 1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 50

His Ala Lys Ile Arg
 1               5

<210> SEQ ID NO 51
```

```
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 51

Val Val Lys Met Arg
 1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 52

Pro Val Lys Met Arg
 1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 53

Val Pro Lys Gln Arg
 1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 54

Val Pro Lys Met Arg
 1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 55

Val Arg Lys Leu Arg
 1               5

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 56

Ser Arg Trp Leu Glu
```

```
<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 57

Phe Arg Trp Leu Glu
 1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 58

Gln Pro Trp Leu Thr
 1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 59

Pro Pro Trp Leu Ile
 1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 60

Pro Pro Trp Leu Lys
 1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 61

Pro Ala Trp Leu Thr
 1               5

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence
```

```
<400> SEQUENCE: 62

Pro Ala Trp Leu Ala
  1               5

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 63

Trp Ala Trp Leu Asp
  1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 64

Pro Thr Trp Leu Thr
  1               5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 65

Glu Glu Val Ser Arg
  1               5

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 66

Glu Tyr Leu Glu Ser
  1               5

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 67

Asp Tyr Val Thr Gln
  1               5

<210> SEQ ID NO 68
<211> LENGTH: 5
<212> TYPE: PRT
```

```
<213> ORGANISM: Artificial Sequence
<220> FEATURE:
<223> OTHER INFORMATION: Description of Artificial Sequence:
      sequential block reoptimization sequence

<400> SEQUENCE: 68

Asp Tyr Leu Ala Asp
1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 69

Glu Tyr Leu Thr Phe
1               5

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 70

Gln Tyr Leu Glu Asp
1               5

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 71

Asp Tyr Val Ser Gln
1               5

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 72

Ser Tyr Leu Asp Lys
1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 73

Glu Tyr Met Ser Asp
1               5
```

```
<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 74

Leu Leu Leu Leu Arg
 1               5

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 75

Met Arg Leu Trp Arg
 1               5

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 76

Met Arg Gly Trp Lys
 1               5

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 77

Met Arg Lys Trp Arg
 1               5

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 78

Met Arg Lys Trp Lys
 1               5

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence:
      sequential block reoptimization sequence

<400> SEQUENCE: 79
```

```
Met Gly Val Met Arg
  1               5
```

<210> SEQ ID NO 80
<211> LENGTH: 27
<212> TYPE: PRT
<213> ORGANISM: Artificial Sequence
<220> FEATURE:
<223> OTHER INFORMATION: Description of Artificial Sequence: ZIF1

<400> SEQUENCE: 80

```
Pro Tyr Ala Cys Pro Val Glu Ser Cys Asp Arg Arg Phe Ser Arg Ser
  1               5                  10                  15

Asp Glu Leu Thr Arg His Ile Arg Ile His Thr
             20                  25
```

<210> SEQ ID NO 81
<211> LENGTH: 28
<212> TYPE: PRT
<213> ORGANISM: Artificial Sequence
<220> FEATURE:
<223> OTHER INFORMATION: Description of Artificial Sequence: GLI1

<400> SEQUENCE: 81

```
Glu Thr Asp Cys Arg Trp Asp Gly Cys Ser Gln Glu Phe Asp Ser Gln
  1               5                  10                  15

Glu Gln Leu Val His His Ile Asn Ser Glu His Ile
             20                  25
```

<210> SEQ ID NO 82
<211> LENGTH: 30
<212> TYPE: PRT
<213> ORGANISM: Artificial Sequence
<220> FEATURE:
<223> OTHER INFORMATION: Description of Artificial Sequence: GLI2

<400> SEQUENCE: 82

```
Glu Phe Val Cys His Trp Gly Gly Cys Ser Arg Glu Leu Arg Pro Phe
  1               5                  10                  15

Lys Ala Gln Tyr Met Leu Val Val His Met Arg Arg His Thr
             20                  25                  30
```

<210> SEQ ID NO 83
<211> LENGTH: 27
<212> TYPE: PRT
<213> ORGANISM: Artificial Sequence
<220> FEATURE:
<223> OTHER INFORMATION: Description of Artificial Sequence: SWI5

<400> SEQUENCE: 83

```
Thr Phe Glu Cys Leu Phe Pro Gly Cys Thr Lys Thr Phe Lys Arg Arg
  1               5                  10                  15

Tyr Asn Ile Arg Ser His Ile Gln Thr His Leu
             20                  25
```